(12) United States Patent
Lewis et al.

(10) Patent No.: US 6,828,029 B1
(45) Date of Patent: Dec. 7, 2004

(54) ZWITTERIONIC GROUPS CONTAINING COMPOUNDS FROM MICHAEL-TYPE REACTIONS USEFUL AS MONOMERS AND MACROMERS

(75) Inventors: Andrew Lennard Lewis, Surrey (GB); Richard Paul Redman, Surrey (GB)

(73) Assignee: Biocompatibles UK Limited, Surrey (GB)

( * ) Notice: Subject to any disclaimer, the term of this patent is extended or adjusted under 35 U.S.C. 154(b) by 0 days.

(21) Appl. No.: 10/203,212

(22) PCT Filed: Sep. 15, 2000

(86) PCT No.: PCT/GB00/03557

§ 371 (c)(1),
(2), (4) Date: Oct. 4, 2002

(87) PCT Pub. No.: WO01/57047

PCT Pub. Date: Aug. 9, 2001

(30) Foreign Application Priority Data

Feb. 7, 2000 (EP) .............................................. 00300943

(51) Int. Cl.$^7$ ............................................... B32B 25/20
(52) U.S. Cl. .......................... 428/446; 623/4.1; 528/28; 528/26; 525/479; 525/404; 427/384; 427/387
(58) Field of Search ................................ 428/447, 457; 427/384, 387; 623/4.1; 528/28, 26; 525/479, 404

(56) References Cited

U.S. PATENT DOCUMENTS

| | | | |
|---|---|---|---|
| 4,348,329 | A | 9/1982 | Chapman |
| 4,507,466 | A | 3/1985 | Tomalia et al. |
| 5,380,904 | A | 1/1995 | Chapman et al. |
| 5,453,467 | A | 9/1995 | Bamford et al. |
| 5,556,710 | A | 9/1996 | Russell et al. |
| 5,645,883 | A | 7/1997 | Russell et al. |
| 5,648,442 | A | 7/1997 | Bowers et al. |
| 5,717,047 | A | 2/1998 | Russell et al. |
| 5,792,827 | A | 8/1998 | Hintze-Bruning et al. |
| 6,177,511 | B1 | 1/2001 | Dauth et al. |
| 6,420,453 | B1 | 7/2002 | Bowers et al. |

FOREIGN PATENT DOCUMENTS

| | | |
|---|---|---|
| EP | 0 274 112 A2 | 7/1988 |
| EP | 0 444 827 A1 | 9/1991 |
| EP | 0 455 585 A1 | 11/1991 |
| EP | 0 713 894 A2 | 5/1996 |
| EP | 0 818 479 A2 | 1/1998 |
| EP | 0 844 268 A1 | 5/1998 |
| EP | 0 933 399 A1 | 8/1999 |

OTHER PUBLICATIONS

U.S. patent application No. 10/203,203.*
M.T. Nowak, "High Solids Coatings–Formulation Aspects", *High Solids Coat.*, (Sep. 1982), pp. 23–28.
Kwiatkowski et al., "A Synthesis of N–Substituted β–Alanines: Michael Addition of Amines to Trimethylsilyl Acrylate," *Synthesis*, (1989), issue 12, pp. 946–949.
Cabral et al., "Catalysis of the Specific Michael Addition: The Example of Acrylate Acceptors," *Tetrahedron Letters*, (1989), vol. 30, No. 30, pp. 3969–3972.

* cited by examiner

Primary Examiner—Kuo-Liang Peng
(74) Attorney, Agent, or Firm—Sughrue Mion, PLLC

(57) ABSTRACT

A zwitterion containing an adduct having the formula (I) wherein Z is a zwitterionic group; X is an electron withdrawing group selected from the group consisting of carbonyl and sulphone groups, sulphonium and phosphonium salts; R is a difunctional organic group; A is O or $NR^6$ where $R^6$ is hydrogen or lower alkyl; $R^1$ and $R^2$ are independently selected from hydrogen and $C_1$–$C_{12}$ alkyl groups; and $R^3$ is hydrogen or an organic group; $R^4$ is an organic group, preferably an optionally substituted alkyl group, an organopolysiloxane group, an organosilyl group or an oligo alkoxyalkyl group. The invention additionally provides processes for the production of such an adduct, polymers formed therefrom, coating processes and compositions comprising an adduct or polymers produced therefrom.

(I)

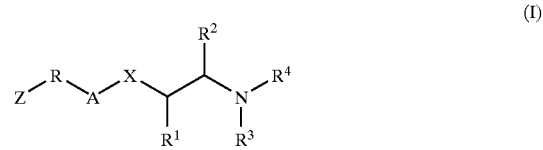

53 Claims, No Drawings

ZWITTERIONIC GROUPS CONTAINING COMPOUNDS FROM MICHAEL-TYPE REACTIONS USEFUL AS MONOMERS AND MACROMERS

Phospholipids are phosphate diester compounds, naturally found in the cell membrane, in which one of the alcohol residues is generally a glycerol derivative, and the other is a derivative of a different alcohol which may include a non-ionic, cationic or even an anionic functionality. Phospholipid and phospholipid analogues are of increasing interest, for example to impart the useful properties of biocompatibility, haemocompatibility and to influence the interaction of surfaces with biomolecules such as proteins or enzymes.

Our previous disclosures such as EP-A 0032622, EP-A-0157469, EP-A-0555295, EP-A-0601041, EP-A-0593561, EP-A-00639989, WO-A-9416748 and WO-A-9416749 describe various synthetic zwitterionic compounds including phospholipid analogues and their application in devices having biocompatible and haemocompatible surfaces. The present invention extends this methodology to new polymer systems comprising monomers and macromers produced by a Michael-type addition.

It is well known in the literature that amines undertake nucleophilic attack on the a, unsaturated carbonyl of an acrylate functionality, resulting in a Michael-type 1,4-adduct (Recent stereoselective synthetic approaches to -amino acids. Cole, Derek C., *Tetrahedron* (1994), 50(32), 9517–82).

This technology has been applied in the preparation of a range of curable coatings (Addition products, radiation-curable surface coating compositions based on the addition products, and their use for wood coating and paper coating, Hintze-Bruning, Horst; Cibura, Klaus; Baltus, Wolfgang, U.S. Pat. No. 5,792,827; High-solids coatings—formulation aspects. Nowak, Michael T. USA. High Solids Coat. (1982), 7(3), 23–8) or resins (Curing agents for liquid epoxy resins, and curable polymer compositions containing them. Shiono, Kenji; Suzuki, Takehiro. JP 09291135; A process for preparation of room-temperature-curable resins. Furukawa, Hisao; Kawamura, Jo., EP 274112).

It has also been used extensively in polymer science, for example, to produce a variety of polymer hybrids (Conductive wire coating based on a curable acrylate-modified amine-terminated polyamide. Frihart, Charles R.; Kliwinski, Joseph. WO 9724191; A polylactone having amino groups, its preparation, and coating and printing ink compositions containing it. Matsui, Hideki, EP 713894; Grafting of amine-functional polymers onto functionalized oxymethylene polymers and the resulting graft polymers thereof. Auerbach, Andrew B.; Broussard, Jerry A.; Yang, Nan L.; Paul, James L. EP 400827) or to build dendrimer structures (Dense star polymers. Tomalia, Donald A.; Dewald, James R. WO 8402705).

It can also be used to functionalise biologically active amine-bearing compounds (A synthesis of N-substituted-alanines: Michael addition of amines to trimethylsilyl acrylate. Kwiatkowski, Stefan; Jeganathan, Azhwarsamy; Tobin, Thomas; Watt, David S. Maxwell H. *Synthesis* (1989), Issue 12, 946–9). In EP-A-0933399 polysiloxane compounds having at least one aminoalkyl substituent on a silicon atom are cross-linked by reaction with di- or oligo-acrylate compounds, optionally in the presence of other acrylic compounds. One example of a substituted acrylic compound which could be incorporated is N,N-dimethyl-N-methacryloxyethyl-N-3-sulphopropyl)-ammonium betaine.

In some of the prior art the reaction may be carried out with either acrylate or methacrylate, although the former is generally preferred in the literature on reactivity grounds. The reaction proceeds usually without catalysis, although there are reports of catalysts to promote solely 1,4 addition in good yields (Catalysis of the specific Michael addition: the example of acrylate acceptors. Cabral, Jose; Laszlo, Pierre; Mahe, Loic; Montaufier, Marie Therese; Randriamahefa, S. Lalatiana., *Tetrahedron Lett.* (1989), 30(30), 3969–72).

The present invention relates to new polymers, processes for producing them, processes for coating surfaces with them and polymer compositions. The invention also provides new prepolymers and processes for their production.

Such polymers are particularly useful in the manufacture or coating of devices with medical applications such as blood contacting devices, contact and intraocular lenses, and other devices which are used in contact with protein-containing or biological fluids.

The present invention provides a zwitterion containing Michael-type adduct having the formula (I)

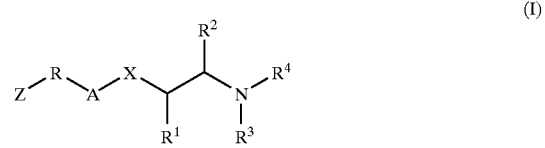

wherein

Z is a zwitterionic group;

X is an electron withdrawing group selected from the group consisting of carbonyl and sulphone groups, sulphonium and phosphonium salts;

R is selected from the group consisting of linear and branched alkanediyl, alkenediyl, alkynediyl, cycloalkanediyl, cycloalkenediyl, cycloalkynediyl, arylene, alkarylene, aralkylene, alkoxyarylene, alkoxyalkyl, oligo(alkoxy)alkyl, mono- and di-alkylaminoalkyl N-arylaminoalkyl, N-aryl-N-alkylaminoalkyl;

$R^1$ and $R^2$ are independently selected from hydrogen and $C_1$–$C_{12}$ alkyl groups;

A is O or $NR^6$, where $R^6$ is selected from the group consisting of hydrogen and $C_{1-6}$ alkyl.

$R^3$ is selected from the group consisting hydrogen, linear and branched alkyl, alkenyl, and alkynyl groups, alkoxycarbonyl, alkylaminocarbonyl, cycloalkyl, cycloalkenyl, cycloalkynyl, haloaryl, haloalkyl, aryl, alkaryl, aralkyl, alkoxyaryl, alkoxyalkyl, oligoalkoxyalkyl, aminoalkyl, mono- and di-alkylaminoalkyl, arylaminoalkyl, N-aryl-N-alkylaminoalkyl and -aminoaryl, acyloxy, acyloxyalkyl, acylaminoalkyl, N-diacyl-iminoalkyl groups, mono- and di-alkylaminocarbonyl, organosilyl, arylamino carbonyl, aryl(alkyl)amino carbonyl, and organosiloxyl groups and any of the above groups substituted with a reactive group, a group $NHCOOR^5$ in which $R^5$ is selected from the group consisting hydrogen, linear and branched alkyl, alkenyl, and alkynyl groups, cycloalkyl, cycloalkenyl, cycloalkynyl, haloaryl, haloalkyl, aryl, alkaryl, aralkyl, alkoxyaryl, alkoxyalkyl, oligoalkoxyalkyl, aminoalkyl, mono- and di-alkylaminoalkyl, arylaminoalkyl, N-aryl-N-alkylaminoalkyl and aminoaryl, acyloxyalkyl, acylaminoalkyl, N-diacyl-iminoalkyl groups, hydroxyalkyl, hydroxyalkenyl, hydroxyalkynyl, hydroxyaryl, hydroxyalkoxyalkyl and hydroxy (oligoalkoxy)alkyl;

a group —NHCONR$^7$R$^8$ in which R$^7$ and R$^8$ are selected from the group consisting hydrogen, linear and branched alkyl, alkenyl, and alkynyl groups, cycloalkyl, cycloalkenyl, cycloalkynyl, haloaryl, haloalkyl, aryl, alkaryl, aralkyl, alkoxyaryl, alkoxyalkyl, oligoalkoxyalkyl, aminoalkyl, mono- and di-alkylaminoalkyl, arylaminoalkyl, N-aryl-N-alkylaminoalkyl and aminoaryl, acyloxyalkyl, acylaminoalkyl, N-diacyl-iminoalkyl groups, hydroxyalkyl, hydroxyalkenyl, hydroxyalkynyl, hydroxyaryl, hydroxyalkoxyalkyl and hydroxy (oligoalkoxy)alkyl; or a polymeric moiety; and R$^4$ is selected from the group consisting hydrogen, linear and branched alkyl, alkenyl, and alkynyl groups, alkoxycarbonyl, alkylaminocarbonyl, cycloalkyl, cycloalkenyl, cycloalkynyl, haloaryl, haloalkyl, aryl, alkaryl, aralkyl, alkoxyaryl, alkoxyalkyl, oligoalkoxyalkyl, aminoalkyl, mono- and di-alkylaminoalkyl, arylaminoalkyl, N-aryl-N-alkylaminoalkyl and -aminoaryl, acyloxy, acyloxyalkyl, acylaminoalkyl, N-diacyl-iminoalkyl groups, mono- and di-alkylaminocarbonyl, organosilyl, arylamino carbonyl, aryl(alkyl)amino carbonyl, and organosiloxyl groups and any of the above groups substituted with a group II

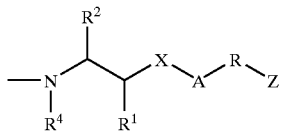

(II)

in which the groups R, R$^1$, R$^2$. R$^4$, Z and A are the same as in (I);

a group III

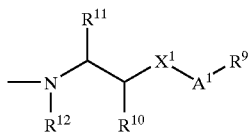

(III)

in which

A$^1$ is O or NR$^{13}$ where R$^{13}$ is hydrogen or C$_{1-4}$ alkyl;

X$^1$ is an electron withdrawing group selected from carbonyl, sulphonyl, sulphonium and phosphonium groups;

R$^{12}$ is H or C$_{1-6}$ alkyl;

R$^{10}$ and R$^{11}$ are independently selected from H and C$_{1-4}$ alkyl; and R$^9$ is optionally substituted alkyl or aryl;

a reactive group; or.

a polymeric moiety.

In the definition of R$^3$, and R$^4$, and any of the groups below any alkyl group or moiety is preferably C$_{1-18}$ alkyl, any alkenyl group or moiety is preferably C$_{2-18}$ alkenyl, any alkynyl group or moiety is preferably C$_{2-12}$ alkynyl, any aryl group or moiety is preferably C$_{6-24}$ aryl, any alkaryl group or moiety is preferably C$_{7-24}$ alkaryl and any aralkyl group or moiety is preferably C$_{7-24}$ aralkyl, any cycloalkyl group or moiety is preferably C$_{4-24}$ cycloalkyl, any cycloalkenyl group or moiety is preferably C$_{5-24}$ cycloalkenyl, any cycloalkynyl group or moiety is preferably C$_{5-24}$ cycloalkynyl.

The zwitterionic group Z preferably has the general formula (IV)

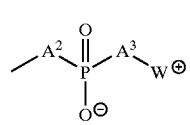

(IV)

in which the moieties A$^2$ and A$^3$, which are the same or different, are —O—, —S—, —NH— or a valence bond, preferably —O—, and W$^+$ is a group comprising an ammonium, phosphonium or sulphonium cationic group and a group linking the anionic and cationic moieties which is preferably a C$_{1-12}$-alkanediyl group, preferably in which W$^+$ is a group of formula —W$^1$—N$^+$R$^{14}$$_3$, —W$^1$—P$^+$R$^{15}$$_3$, —W$^1$—S$^+$R$^{15}$$_2$ or —W$^1$—Het$^+$ in which:

W$^1$ is alkanediyl of 1 or more, preferably 2–6 carbon atoms optionally containing one or more ethylenically unsaturated double or triple bonds, disubstituted-aryl (arylene), alkylene arylene, arylene alkylene, or alkylene aryl alkylene, cycloalkanediyl, alkylene cycloalkyl, cycloalkyl alkylene or alkylene cycloalkyl alkylene, which group W$^1$ optionally contains one or more fluorine substituents and/or one or more functional groups; and either the groups R$^{14}$ are the same or different and each is hydrogen 2 D or alkyl of 1 to 4 carbon atoms, preferably methyl, or aryl, such as phenyl, or two of the groups R$^{14}$ together with the nitrogen atom to which they are attached form an aliphatic heterocyclic ring containing from 5 to 7 atoms, or the three groups R$^{14}$ together with the nitrogen atom to which they are attached form a fused ring structure containing from 5 to 7 atoms in each ring, and optionally one or more of the groups R$^{14}$ is substituted by a hydrophilic functional group, and the groups R$^{15}$ are the same or different and each is R$^{14}$ or a group OR$^{14}$, where R$^{14}$ is as defined above; or Het is an aromatic nitrogen-, phosphorus- or sulphur-, preferably nitrogen-, containing ring, for example pyridine.

Most preferably the zwitterionic group of the formula (IV), has the general formula (V):

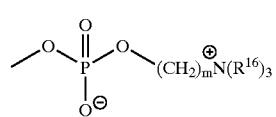

(V)

where the groups R$^{16}$ are the same or different and each is hydrogen or C$_{1-4}$ alkyl, and m is from 1 to 4, preferably 2. Preferably the groups R$^{16}$ are the same and are preferably methyl.

Alternatively, the zwitterionic group may be a betaine group (ie. in which the cation is closer to the backbone), for instance a sulpho-, carboxy- or phospho-betaine. A betaine group should have no overall charge and Is preferably therefore a carboxy- or sulphobetaine. If it is a phosphobetaine the phosphate terminal group must be a diester, i.e., be esterified with an alcohol. Such groups may be represented by the general formula (IV)

 (VI)

in which $A^4$ is a valence bond, —O—, —S— or —NH—, preferably —O—;

V is a carboxylate, sulphonate or phosphate diester (monovalently charged) anion;

$R^{17}$ is a valence bond (together with $A^4$) or alkanediyl, C(O)alkylene- or —C(O)NHalkylene preferably alkanediyl, and preferably containing from 1 to 6 carbon atoms in the alkanediyl chain;

the groups $R^{18}$ are the same or different and each is hydrogen or alkyl of 1 to 4 carbon atoms or the groups $R^{18}$ together with the nitrogen to which they are attached form a heterocyclic ring of 5 to 7 atoms; and $R^{19}$ is alkyanediyl of 1 to 20, preferably 1 to 10, more preferably 1 to 6 carbon atoms.

One preferred sulphobetaine monomer has the formula (VII)

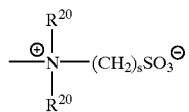 (VII)

where the groups $R^{20}$ are the same or different and ach is hydrogen or $C_{1-4}$ alkyl and s is from 2 to 4.

Preferably the groups $R^{20}$ are the same. It is also preferable that at least one of the groups $R^{20}$ is methyl, and more preferable that the groups $R^{20}$ are both methyl.

Preferably s is 2 or 3, more preferably 3.

Alternatively the zwitterionic group may be an amino acid moiety in which the alpha carbon atom (to which an amine group and the carboxylic acid group are attached) is joined through a linker group to the backbone of the biocompatible polymer. Such groups may be represented by the general formula (VIII)

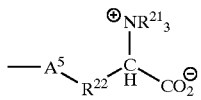 (VIII)

in which $A^5$ is a valence bond, —O—, —S— or —NH—, preferably —O—, $R^{22}$ is a valence bond (optionally together with $A^5$) or alkanediyl, —C(O)alkylene- or —C(O)NHalkylene, preferably alkanediyl and preferably containing from 1 to 6 carbon atoms; and the groups $R^{21}$ are the same or different and each is hydrogen or alkyl of 1 to 4 carbon atoms, preferably methyl, or two or three of the groups $R^{21}$, together with the nitrogen to which they are attached, form a heterocyclic ring of from 5 to 7 atoms, or the three group $R^{21}$ together with the nitrogen atom to which they are attached form a fused ring heterocyclic structure containing from 5 to 7 atoms in each ring.

X is preferably a carbonyl group.

A is preferably 0

$R^1$ is preferably hydrogen.

$R^2$ is preferably methyl, or, more preferably, hydrogen.

R is preferably $C_{2-6}$-alkanediyl.

$R^3$ is preferably hydrogen, or is an optionally substituted alkyl aminocarbonyl or arylaminocarbonyl group.

In a preferred embodiment $R^3$ is a hydrog n atom or comprises a reactive group. Reactive groups include, for example, groups containing an ionic group or a site of unsaturation that is capable of forming a covalent bond with another group or to a substrate. Alternatively the reactive group may increase the ability of the adduct to physisorb or chemisorb to another group or to a substrate relative to the ability of the adducts to physisorb or chemisorb exclusive of the reactive group.

Preferred substrates include, for example, silicones, polyurethanes, polyalkacrylates, polystyrenes, polycarbonates, polyesters and metals (particularly stainless steel).

Other groups with which the reactive group may bond, physisorb or chemisorb to include, for example, another adduct (I) or polymer formed by polymerisation of adduct (1), polymers having desirable physical or mechanical properties, drugs, ligands or biological molecules such as enzymes or heparin.

Where $R^3$ comprises a reactive group, it preferably comprises at least one group selected from the group consisting of isocyanate, organosilane and (meth)acryloyloxy.

Most preferably a group $R^3$ which contains a reactive group is an cycloalkylaminocarbonyl, arylaminocarbonyl, or alkylaminocarbonyl group containing an isocyanate substituent.

$R^4$ is preferably, other than hydrogen, more preferably an organopolysiloxane group, an oligoalkoxyalkyl group, an organosilyl group or a $C_{6-24}$ alkyl group.

An organosiloxyl group Y utilised in the present invention, for example as $R^4$, preferably has the formula (IX)

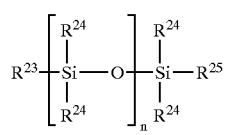 (IX)

in which at least one of the groups $R^{23}$, $R^{24}$ and $R^{25}$ is a divalent moiety selected from the group consisting of a valence bond, $C_{1-12}$ alkanediyl, $C_{2-12}$ alken diyl and $C_{2-12}$ alkynediyl and is covalently bonded to the nitrogen atom of adduct (I) and the remaining groups $R^{23}$, $R^{24}$ and $R^{25}$ each represent a monovalent moiety independently selected from the group consisting of branched and straight $C_{1-12}$ alkyl, $C_{6-18}$ aryl, $C_{6-18}$ alkaryl, $C_{6-18}$ aralkyl, $C_{2-12}$ alkenyl and $C_{2-12}$ alkynyl any of which may be substituted by a primary, secondary or tertiary amine group or by a group III as defined in claim 1; and n is 0–300.

Preferably IX has a molecular weight of 300–20000, for instance 500–10000, more preferably 1000–7000, most preferably 3000–6000.

Preferably $R^{23}$ and $R^{25}$ are selected from methanediyl, ethanediyl, propanediyl and butanediyl, and are both covalently bound to the nitrogen atom of individual adducts (I).

Alternatively, or in addition to both $R^{23}$ and $R^{25}$ being connected to adducts (1), one or more of the groups $R^{24}$ may comprise a —$NR^{26}_2$ substituent where each $R^{26}$ is independently selected from hydrogen or $C_{1-6}$ alkyl and aryl, or a substituent of the formula III as defined above.

In preferred embodiments adduct (I) has one of the formula (X), (XI), (XII), (XIII), or (XIV)

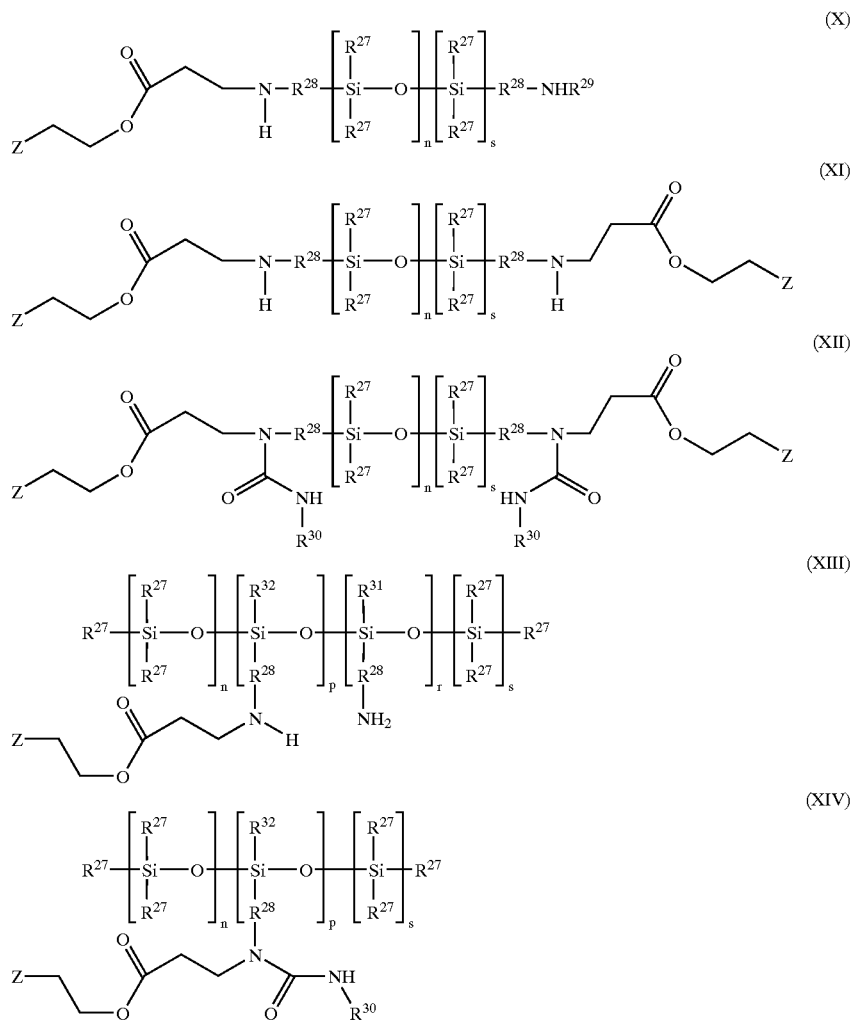

wherein each of the of the groups $R^{27}$ is independently selected from the group consisting of $C_{1-6}$ alkyl, $C_{6-18}$ aryl, $C_{6-18}$ alkyl, $C_{6-18}$ alkaryl, and $C_{2-6}$ alkenyl, preferably $C_{1-6}$ alkyl, most preferably methyl or ethyl;

the or each $R^{28}$ is independently selected from the group consisting of $C_{1-6}$ alkanediyl, $C_{2-6}$ alkendiyl and $C_{2-6}$ alkynediyl, preferably $C_{1-6}$ alkanediyl;

$R^{31}$ is selected from the same groups as $R^{27}$ or is a group $R^{28}NH_2$;

$R^{32}$ is selected from the same groups as $R^{27}$ or is a group $R^{28}NH_2$ or a group $R^{28}NH(CH_2)_2COO(CH_2)_2$ Z or a group $-R^{28}N(CONHR^{30})CH_2CH_2COO(CH_2)_2Z$;

$R^{29}$ is selected from the group consisting of hydrogen, $C_{1-6}$ alkyl, $C_{6-18}$ aryl, $C_{6-18}$ aralkyl, $C_{2-6}$ alkenyl, $C_{6-18}$ alkaryl, preferably hydrogen or $C_{1-4}$alkyl;

each $R^{30}$ is independently selected from the group consisting hydrogen, linear and branched alkyl, alkenyl, and alkynyl groups, alkoxycarbonyl, alkylaminocarbonyl, cycloalkyl, cycloalkenyl, cycloalkynyl, haloaryl, haloalkyl, aryl, alkaryl, aralkyl, alkoxyaryl, alkoxyalkyl, oligoalkoxyalkyl, aminoalkyl, mono-, di- and tri-alkylaminoalkyl, arylaminoalkyl; N-aryl-N-alkylaminoalkyl and -aminoaryl, acyloxy (including alkenoyloxy), acyloxyalkyl (including alkenoyloxyalkyl), acylaminoalkyl, N-diacyl-iminoalkyl groups, alkylaminocarbonyl, organosilyl and organosiloxyl groups and any of the above groups substituted with a zwitterionic group Z or an isocyanate group;

n is an integer of 1 to 500;
p is an int ger of 1 to 50;
r is an integer of 1 to 50; and
s is 0 or 1 (preferably 1).

The formula (XIII) and (XIV) are not intended to represent the specific order within the organosiloxane backbone of the groups [—O—SiR$^{27}_2$], [—O—SiR$^{32}$R$^{28}$ . . . ] and [—O—SiR$^{31}$(R$^{28}$ . . . )], and in fact these groups can be randomly or specifically ordered within the backbone.

Most preferably all groups $R^{27}$, $R^{31}$ and $R^{32}$, are methyl and $R^{28}$ is selected from 1,2-ethanediyl, 1,3-propanediyl and 1,4-butanediyl.

Alternatively, $R^4$ may comprise a polyoxyalkylene group having the formula (XV)

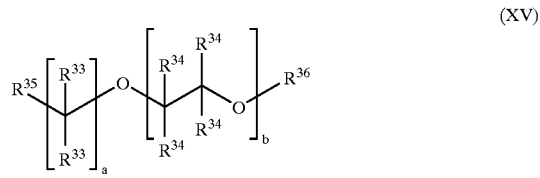

(XV)

wherein each group $R^{33}$ is independently selected from the group consisting of hydrogen, $C_{1-6}$ alkyl $C_{6-18}$ aryl, $C_{6-18}$ aralkyl, $C_{6-18}$ alkaryl and $C_{2-6}$ alkenyl;

each group $R^{34}$ is independently selected from the group consisting of hydrogen, $C_{1-6}$ alkyl, $C_{6-18}$ aryl, $C_{6-18}$ aralkyl, $C_{6-18}$ alkaryl and $C_{2-8}$ alkenyl;

$R^{35}$ is a divalent moiety selected from the group consisting of a valence bond, $C_{1-6}$ alkanediyl, $C_{6-18}$ arylene, $C_{6-18}$ aralkylene, $C_{2-8}$alkenediyl, mono-, di- and tri-alkylaminoalkyl, arylaminoalkyl, arylaminoaryl, N-aryl-N-alkylaminoalkyl and -aminoaryl;

$R^{36}$ is a divalent moiety selected from the same groups as $R^{35}$ or is a monovalent moiety selected from the same groups as $R^{33}$, aminoalkyl and aminoaryl, and alkyl and aryl groups substituted by groups of general formula II or III as defined in claim 1;

a is 0 or an integer in the range 1–10, b is 0 or an integer of in the range 1–500; and (XV) has a formula weight of 100–10000.

Each group $R^{34}$ is preferably selected from hydrogen and $C_{1-4}$ alkyl, and is most preferably methyl or, most preferably hydrogen. For instance one of the groups $R^{34}$ may be a methyl group and the rest hydrogen, but most preferably all are hydrogen.

Preferably group XV has a formula weight in the range 50–20,000.

In a further preferred embodiment, adduct (I) has the formula (XVI), (XVII) or (XVIII)

wherein each group $R^{33}$ is independently selected from the group consisting of hydrogen, $C_{1-4}$ alkyl, $C_{6-}$aryl, $C_{6-18}$ aralkyl, and $C_{6-18}$ alkaryl;

each group $R^{37}$ is independently selected from the group consisting of hydrogen, $C_{1-4}$ alkyl, $C_{6-18}$ aryl, $C_{6-18}$ aralkyl, and $C_{6-18}$ alkaryl;

each group $R^{34}$ is independently selected from the group consisting of hydrogen, $C_{1-4}$ alkyl, $C_{6-18}$ aryl, $C_{6-18}$ aralkyl, and $C_{6-18}$ alkaryl;

c is 0 or an integer in the range 1 to 10;

$R^{38}$ is selected from the group consisting of hydrogen, $C_{1-4}$alkyl, $C_{6-18}$ aryl, $C_{6-18}$ aralkyl, $C_{6-18}$ alkaryl, and $C_{2-6}$ alkenyl; and each $R^{39}$ is independently selected from the group consisting of hydrogen, linear and branched alkyl, alkenyl, and alkynyl groups, alkoxycarbonyl, alkylaminocarbonyl, cycloalkyl, cycloalkenyl, cycloalkynyl, haloaryl, haloalkyl, aryl, alkaryl, aralkyl, alkoxyaryl, alkoxyalkyl, oligoalkoxyalkyl, aminoalkyl, mono-, di- and tri-alkylaminoalkyl, arylaminoalkyl, N-aryl-N-alkylaminoalkyl and -aminoaryl, acyloxy (including alkenoyloxy), acyloxyalkyl (including alkenoyloxyalkyl), acylaminoalkyl, N-diacyl-iminoalkyl groups, alkylaminocarbonyl, organosilyl and organosiloxyl groups and any of the above groups substituted with a zwitterionic group Z or an isocyanate group.

Preferably each group $R^{34}$ is selected from propyl, ethyl, methyl and hydrogen and are preferably all the same, more preferably hydrogen.

$R^{36}$ is preferably hydrogen.

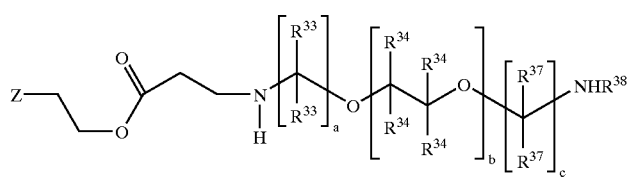

(XVI)

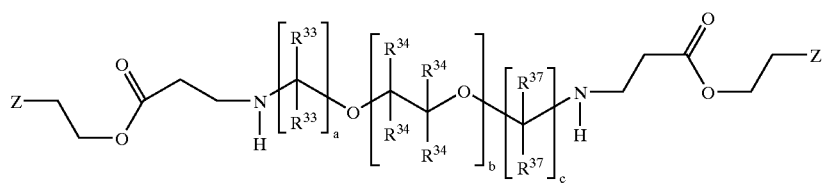

(XVII)

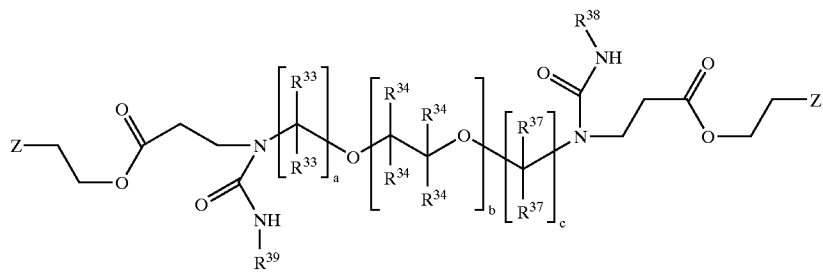

(XVIII)

One preferred organosilane group as $R^4$ or, less preferably, $R^3$, has the general formula (XIX)

(XIX)

wherein each $R^{47}$ is selected from the group consisting of hydrogen, branched and straight $C_{1-12}$ alkyl, $C_{6-18}$ aryl, $C_{6-18}$ alkaryl, $C_{6-18}$ aralkyl, $C_{2-12}$ alkenyl and $C_{2-12}$ alkynyl; $R^{40}$ is selected from the group consisting of a valence bond, branched and straight chain $C_{1-12}$ alkanediyl, straight and branched $C_{2-12}$ alkenediyl and straight and branched $C_{2-12}$ alkynediyl; and (X) is connected to the N atom of (I) through $R^{40}$.

The present invention additionally provides a method for the production of an adduct by the Michael-type addition of a compound having the formula (XX)

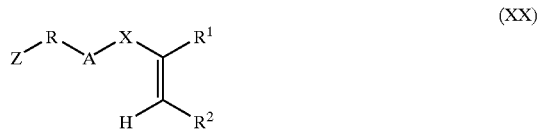
(XX)

with an amine reagent having the formula (XXI)

$H_2NR^{41}$ (XXI)

to form a zwitt rion containing compound having the formula (XXII)

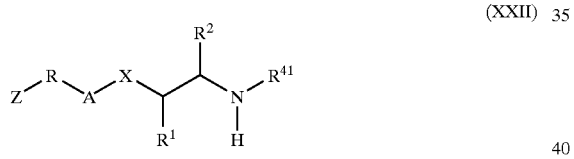
(XXII)

wherein

Z is a zwitterionic group;

A is O or $NR^6$ in which $R^6$ is hydrogen or a $C_{1-4}$ alkyl group;

X is an electron withdrawing group selected from the group consisting of carbonyl and sulphone groups, sulphonium and phosphonium salts;

R is selected from the group consisting of linear and branched alkanediyl, alkenediyl, alkynediyl, cycloalkanediyl, cycloalkenediyl, cycloalkynediyl, arylene, alkarylene, aralkylene, alkoxyarylene, alkoxyalkylene, oligoalkoxyalkylene, mono- or di-alkylaminoalkyl, N-arylamino alkylene, is N-aryl-N-alkylaminoalkylene, $R^{41}$ is selected from the group consisting hydrogen, linear and branched alkyl, alkenyl and alkynyl groups, cycloalkyl, cycloalkenyl, cycloalkynyl, haloaryl, haloalkyl, aryl, alkaryl, aralkyl, hydroxyalkyl, hydroxyaryl, alkoxyaryl, alkoxyalkyl, oligoalkoxyalkyl, acyloxyalkyl, organosilane and organosiloxane groups any of which may be substituted by a group selected from amino, N-alkyl amino, N,N-dialkylamino, N-aryl-N-alkylamino and N-acylamino groups; and $R^1$ and $R^2$ are independently selected from hydrogen and $C_1$–$C_{12}$ alkyl groups.

$R^1$ and $R^2$ are preferably selected from hydrogen or $C_1$–$C_4$ alkyl groups most preferably both are hydrogen.

The structure is not intended to represent that when $R^1$ and $R^2$ are not both hydrogen atoms that are in a cis-configuration about the double bond and in fact they may be trans.

A, Z, R and X have the same preferred definitions as in the adduct of general formula I above.

$R^{41}$ is preferably the respective group from which the preferred $R^4$ groups described above are derived. Often $R^{41}$ includes amino substitutions, whereby the second amine group may take part in a reaction with a zwitterionic reagent of the general formula XX.

One mole of amine reagent may react with up to two moles of zwitterionic reagent. Alternatively the primary or secondary amine derived from the amine reagent may be used to crosslink to or otherwise react with a different group or substrate, either by a Michael type addition or an alternative reaction mechanism, for example, nucleophilic addition or substitution. Simultaneously or after the reaction of the zwitterionic reagent and the amine reagent, some of the amine groups of a di- or oligo-amine reagent (that is in which $R^{41}$ includes one or more amine substituents) may be reacted in a further Michael addition with acrylic reagents of the general formula

(XXVI)

in which $A^1$ is O or $NR^{13}$ where $R^{13}$ is hydrogen or $C_{1-6}$ alkyl;

$X^1$ is an electron withdrawing group selected from carbonyl, sulphonyl, sulphonium and phosphonium groups;

$R^{12}$ is H or $C_{1-6}$ alkyl;

$R^{10}$ and $R^{11}$ are independently selected from H and $C_{1-4}$ alkyl; and $R^9$ is optionally substituted alkyl or aryl.

By carrying out such a further reaction those amine groups of the amine reagent are converted to groups of the general formula III defined above.

Compound (XXII) may undergo a second reaction with an isocyanate reagent (XXIII)

$R^{42}$—N=C=O (XXIII)

wherein $R^{42}$ is selected from the group consisting of linear and branched alkyl, alkenyl, and alkynyl groups, alkoxycarbonyl, cycloalkyl, cycloalkenyl, cycloalkynyl, haloaryl, haloalkyl, aryl, alkaryl, aralkyl, alkoxyaryl, alkoxyalkyl, oligoalkoxyalkyl, di-alkylaminoalkyl, N-aryl-N-alkylaminoalkyl and acyloxy (including alkenoyloxy), acyloxyalkyl (including alkenoyloxyalkyl), N-diacyl-iminoalkyl groups, organosilane and organosiloxane groups and any of the above groups substituted with a zwitterionic group Z or an isocyanate group, to form a compound having the formula (XXIV)

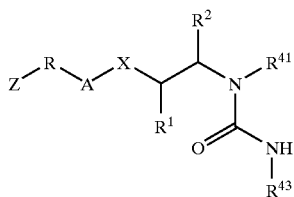

(XXIV)

in which $R^{43}$ is the same as $R^{42}$ or, where $R^{42}$ comprises an isocyanate group, may be the corresponding group formed by reaction of the isocyanate group with a compound having an active hydrogen atom present in the second reaction mixture a hydroxyl group containing compound or a primary or secondary amine group containing compound).

In a preferred embodiment, $R^{42}$ comprises a site of unsaturation, most preferably an isocyanate group or an ethylenic group, capable of crosslinking to another compound of general structure (XX), another polymer or group, or alternatively a substrate as defined hereinbefore. Said site of unsaturation may alternatively provide a site at which homo or co-polymerisation of a compound (XXIV) may occur, for example an ethylenically unsaturated group such as alkenoyloxy.

Most preferably the isocyanate reagent is an isocyanate or diisocyanate and is preferably selected from the group consisting of $C_{2-30}$, aliphatic, $C_{6-30}$ aromatic and $C_{6-20}$ alicyclic isocyanates or diisocyanates $C_{4-30}$ allyl isocyanates, $C_{3-30}$ isocyanatoalkylacrylates, $C_{5-30}$ isocyanato alkylmethacrylates, more preferably preferably allyl isocyanate, dimethyl meta-isopropenylbenzylisocyanate, isophorone diisocyanate, hexamethylene diisocyanate, meta-tetramethylxylylene diisocyanate.

In the reaction of amine with zwitterionic reagent in a preferred embodiment of amine reagent group $R^{41}$ has the general formula XXV

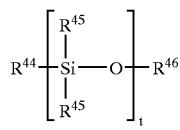

XXV in which one of the groups $R^{44}$ or $R^{45}$ is a divalent moiety selected from the group consisting of a valence bond, $C_{1-12}$-alkanediyl, $C_{2-12}$ alkenediyl, $C_{2-12}$-alkynediyl and the remaining groups $R^{44}$, $R^{45}$ and $R^{46}$ are monovalent moieties independently selected from straight and branched $C_{1-12}$- alkyl, $C_{2-12}$ alkenyl, $C_{2-12}$ alkynyl, $C_{6-24}$ alkanyl, $C_{6-24}$ aryalkyl and aryl, any of which groups may be substituted by one or more amino, N-alkylamino, N,N-dialkylamino, N-alkyl-N-arylamino or N-arylamino groups; and t is 0 to 300.

In such an embodiment preferably $R^{44}$ is a $C_{2-6}$ alkanediyl, each of the groups $R^{45}$ is methyl, $R^{46}$ is an amino substituted $C_{2-6}$ alkyl group and n is in the range 5 to 50.

In another preferred embodiment of the process of the invention, in the amine reagent $R^{41}$ is a group of formula XXVI

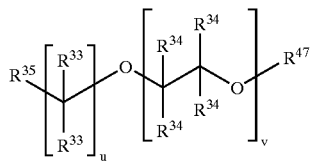

XXVI wherein each group $R^{33}$ is independently selected from the group consisting of hydrogen, $C_{1-6}$ alkyl, $C_{6-18}$ aryl, $C_{6-18}$ aralkyl, $C_{6-18}$ alkaryl end $C_{2-6}$ alkenyl; each group $R^{34}$ is independently selected from the group consisting of hydrogen, $C_{1-4}$ alkyl, $C_{6-18}$ aryl, $C_{6-18}$ aralkyl, $C_{6-18}$ alkaryl and $C_{2-6}$ alkenyl;

$R^{35}$ is a divalent moiety selected from the group consisting of a valence bond, $C_{1-6}$ alkanediyl, $C_{6-18}$ arylene, $C_{6-18}$ aralkylene, $C_{2-6}$ alkenediyl, mono-, di- and trialkylaminoalkyl, arylaminoalkyl, arylaminoaryl, N-aryl-N-alkylaminoalkyl and N-aryl-N-alkylaminoaminoaryl;

$R^{47}$ is selected from the same groups as $R^{33}$, or is $C_{1-12}$ alkyl substituted by an amino, N-alkylamino, N,N-dialkylamino N-arylamino or N-aryl-N-alkylamino group;

u is 0 or an integer in the range 1–10, v is 0 or an integer of in the range 1–500; and XXVI has a formula weight of 100–10000.

The two steps of the preferred reaction may be carried out simultaneously separately. Two separate steps are favoured as this allows work up of a characterisable, pure product after the first step.

The first step (reaction of the zwitterionic reagent with the amine reagent) may be performed in a solventless system when one component is able to solubilise the other. Alternatively, an aqueous or organic solvent may be utilised. Preferred organic solvents include alcohols (including hydroxyalkyl(meth)acrylates), chlorinated hydrocarbons, organosulphoxides, alkylamides and ethers.

Where (I) contains an ester linkage, one prerequisite for the Michael addition step is that the solvent in which the reaction occurs is chosen carefully in order to avoid the possibility of transesterification of the ester linkage in the resulting adduct. Transesterifications are acid or base catalysed reactions and it is likely that the basic structure of the secondary amine in the adduct is sufficient to catalyse the convertion. In particular it is found that the use of methanol as a reaction solvent results in a Michael adduct that has been almost exclusively transesterified, producing the methyl ester of the amine. When isopropylalcohol is used instead of methanol, the trans sterification is virtually eliminated with only traces of the transest rifled product being detected. Acidity, nucleophilicity and steric hinderance of the alcohol group are all considerations in determining whether the solvent system used will be suitable for the Michael addition.

The second step of the reaction with the isocyanate may be carried out in a solventless system or in aqueous or organic solvents. Preferably, where isocyanate or diisocyanates are utilised, the reaction is carried out in the absence of water. As the reaction proceeds an organic solvent is usually required. Preferred organic solvents include alcohols (including hydroxyalkyl(meth)acrylate), chlorinated hydrocarbons, organosulphoxides, alkylamides and ethers.

A particularly preferred solvent for the first reaction is isopropanol or hydroxyethylmethacrylate. For the second reaction, the preferred solvents include dimethylsulphoxide, isopropanol, hydroxyethylmethacrylate, tetrahydrofuran, or N-methylpyrrolidone or mixtures thereof.

Scheme 1 shows two reaction routes resulting in particularly preferred products.
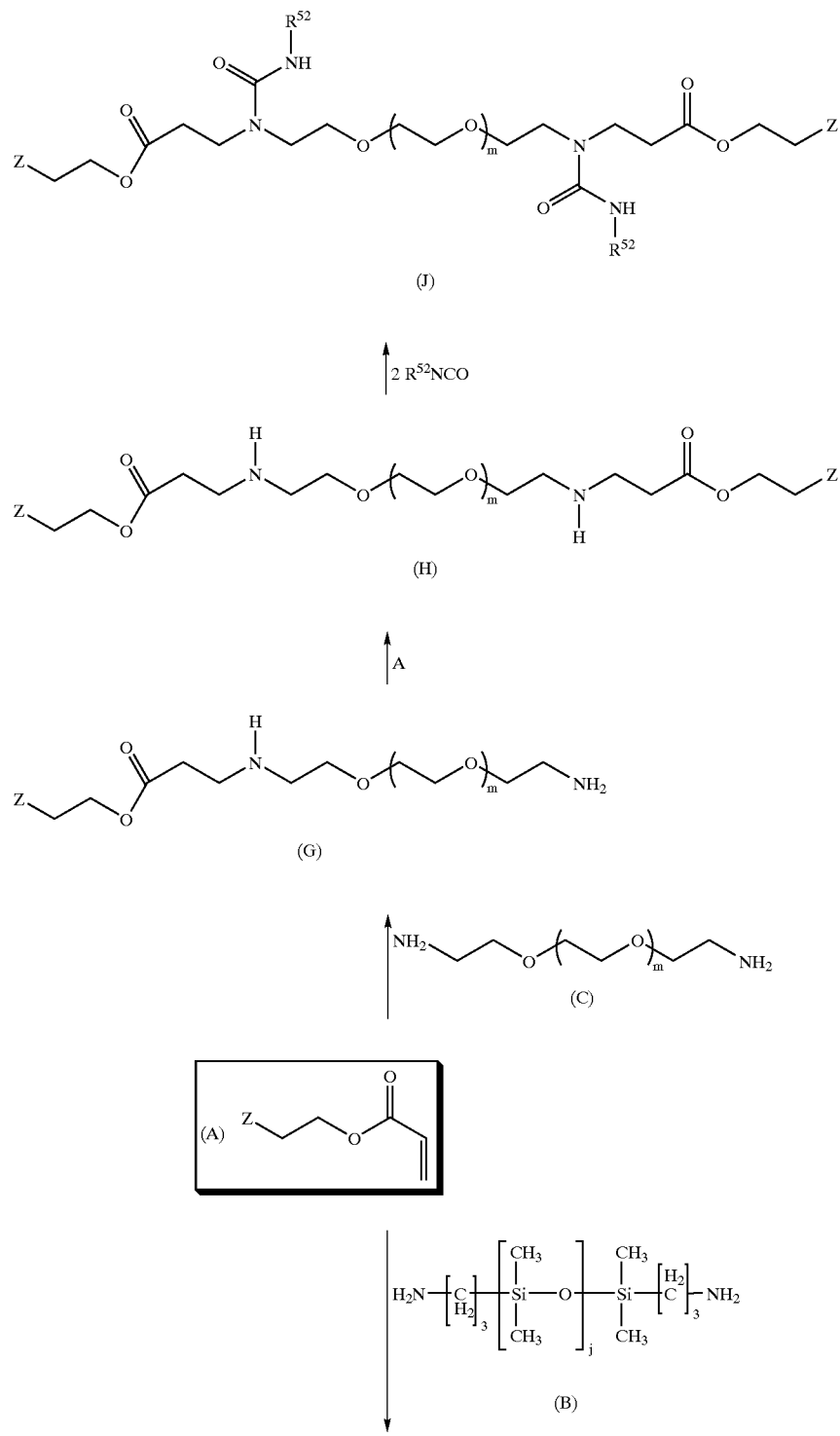

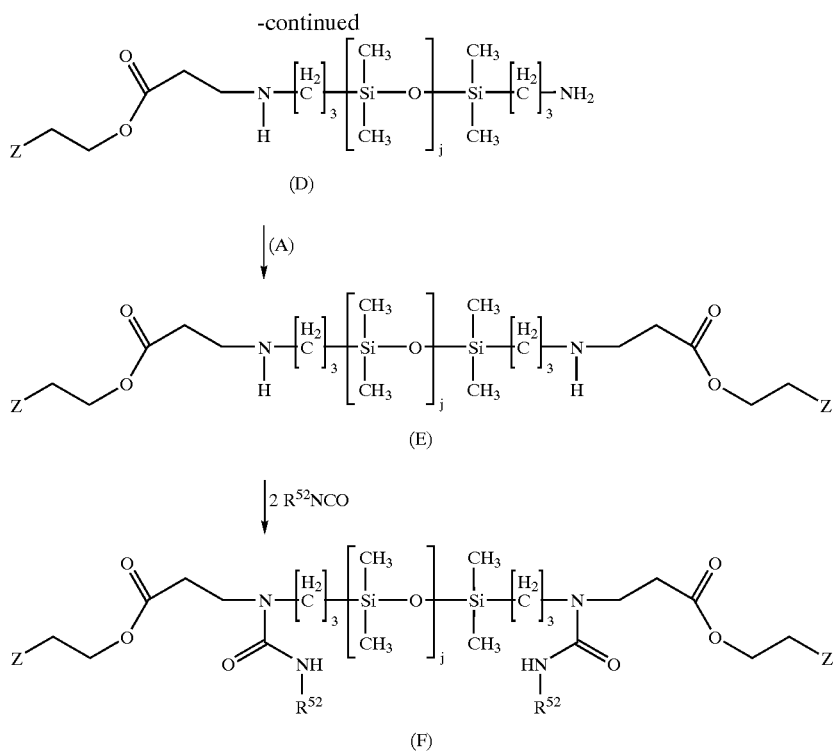

wherein m and ar integers of 10–400.

In both examples (reaction with organosiloxane (B) or polyoxyalkylene) (C)) the first two steps may be carried out separately or concurrently depending on the stoichiometry of the reaction. Preferably the production of (E) or (H) by the zwitterion containing group (A) occurs in one step. The reaction product is preferably recovered and the further step of reaction with a reactive group (in the examples shown, an isocyanate), is carried out.

For example, if a diisocyanate compound is used to functionalise compound (E) or compound (H), this will produce an isocyanate-functionalised oligomer that could form a block in a segmented polyurethane urea.

Scheme 2 illustrates another particularly preferred embodiment of the present invention. Compound (E) (or more generally an intermediate of the general formula (XXII) is reacted with a diisocyanate compound to produce a compound of type (K) having pendant isocyanate groups. This compound can be reacted further with a capping reagent, for example, hydroxyethylmethacrylate or t-butylaminoethyl methacrylate to produce a methacrylate-terminated oligomer (compounds (L) and (M) in scheme 2, ideal for free-radical polymerisation with other ethylenically unsaturated monomers. This could also be achieved in one step if a zwitterion containing Michael adduct is reacted with an isocyanate bearing unsaturation in some form. Particularly useful are isocyanates such as dimethylmeta-isopropenylbenzylisocyanate, allylisocyanate or methacryloloxyethylisocyanate.

Alternatively, or prior to introduction of a cap, compound K, for example, could be reacted with a similar or dissimilar group E, for example. Another amine (either having undergone or not undergone a Michael addition reaction) may be introduced to react with (K) as another way of adding additional entities with desired physical and/or chemical properties into the molecule. The "oth r amine" is typically any diamine for which the ratio of diisocyanate is adjusted such that some chain extension of compound (K) occurs, prior to capping the molecule. The addition of the "other" amine is prior to cap addition and may be accompanied by further diisocyanate addition to maintain stoichiometry.

Scheme 2

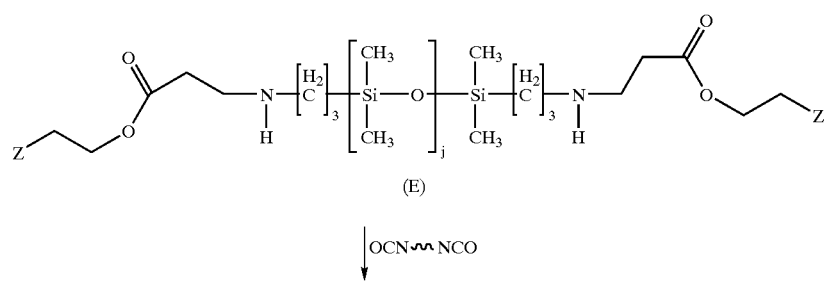

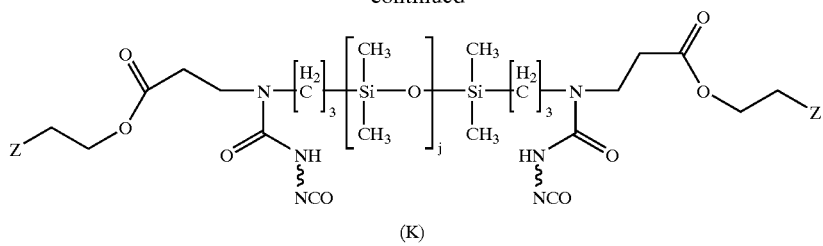

(K)

t-butylaminoethylmethacrylate hydroxyethylmethacrylate

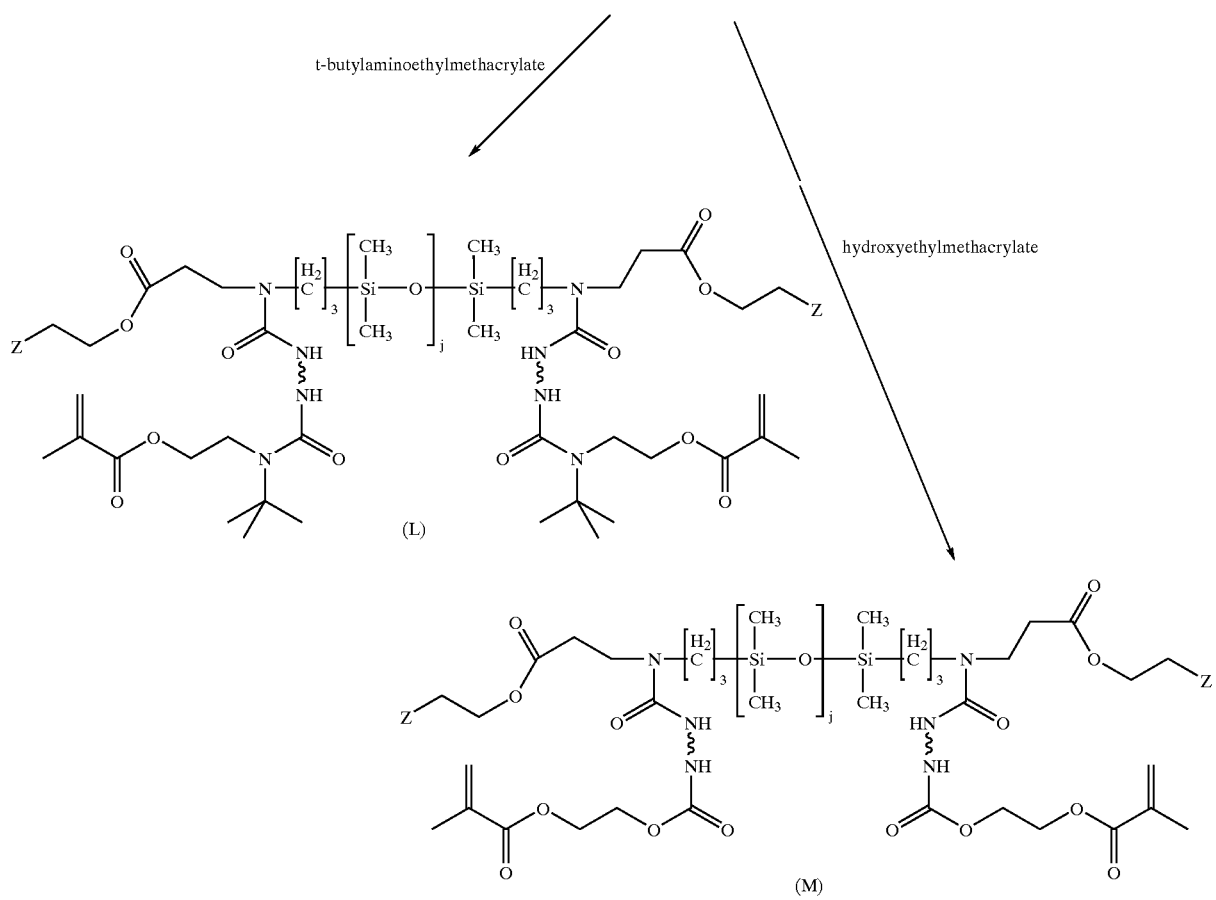

(L)

(M)

Materials comprising the adducts described hereinbefore are of particular utility in medical device manufacture.

In particular, organosiloxane containing adducts, or polymers or copolymers produced by their polymerisation have particular utility in the manufacture of contact and intra ocular lenses. They provide high oxygen permeability and biocompatibility within the ocular environment.

Where the amine reagent of the general formula XXI comprises functional groups in addition to the amine functionality, an adduct formed therefrom can provide products that possess utility as graftable coatings. For example, where the amine reagent comprises pendant reactive groups such as alkyl groups substituted with aldehyde or carboxylic acid groups, adducts (or polymers) formed therefrom may be used to graft onto biological tissue bearing lysine moieties. Alternatively, where an amine is functionalised with an organosilane group such as (XIX), this may be used to graft an adduct of the present invention to an organic or inorganic substrate. Compounds and polymers bearing such an organosilane group show particular utility in bonding to metal surfaces.

The presence of the zwitterionic component in a polymer provided by polymerisation of an adduct of the present invention improves the biocompatibility of the material compared with non-zwitterionic containing analogues. If, for example, it is desirable to make biodegradable materials, this could be achieved by the incorporation of a suitably labile chain extender, the degradation product being less toxic to the body than a similar compound not bearing a zwitterionic group. Similarly, wear-debris from a nondegradable implant or contact lens of the materials should also be of less risk than a similar material not bearing a zwitterionic group to the body or ocular environment.

The production of a polymer comprising an adduct of the present invention may be achieved by any known polymerisation method. As described above, this may be achieved by funtionalising the adduct to incorporate a site of unsaturation, thus providing an adduct capable of, for example, free radical polymerisation.

The present invention additionally incorporates compositions comprising adduct(s) of the present invention, and compositions of polymers produced by polymerisation of such an adduct.

The following examples illustrate the working of the present invention.

Starting Materials:

| Material | Code | Supplier |
|---|---|---|
| Pendant amino-functional PDMS (AEW 1170) | AMS 162 | Apollo |
| Terminal amino-functional PDMS (AEW 810) | DMS A12 | Apollo |
| Terminal amino-functional PDMS (AEW 1265) | DMS A15 | Apollo |
| Terminal amino-functional PEG (AEW 315) (Jeffamine ED 600) | JED 600 | Huntsman |
| Ethylene diamine | ED | Aldrich |
| Allyl isocyanate | AI | Aldrich |
| Dimethyl meta-isopropenyl benzyl isocyanate | TMI | Cytec |
| Isophorone diisocyanate | IPDI | Aldrich |
| Hexamethylene diisocyanate | HMDI | Aldrich |
| Meta-tetramethylxylylene diisocyanate | TMXDI | Cytec |
| Dimethylacrylamide | DMA | Aldrich |
| t-Butylaminoethyl methacrylate | BAM | Aldrich |
| 2-Acryoyloxyethyl phosphorylcholine | APC | Synthesised |
| Isopropanol | IPA | Romil |
| N,N'-Dimethylacrylamide | NNDMA | Aldrich |
| 3-[Tris(trimethylsilyloxy)silyl]propyl methacrylate | TRIS | Aldrich |
| Ethylene glycol dimethacrylate | EGDM | Aldrich |
| Terminal aminofunctional poly(propylene glycol) | D400 | |

PEG refers to polyethyleneglycol and AEW refers to amine equivalent weight The molecular weight (Mw) of AMS 162 is 4000–5000.

All materials were obtained and purified as described in the examples. (2-acryloyloxyethyl)-2'-(trimethyl-ammoniumethyl) phosphate, inner salt (Acryloyl-phosphorylcholine, APC) was made by a modification of the route described previously by Ishihara et al. (*Polym. J.*, 2(3), 355, 1990):

All glassware was dried thoroughly before use. 2-Chloro-2-oxo 1,3,2 dioxaphospholane (CCP, Avocado Chemical Co.) (68.3 g, 0.48 mol, 1.05 equiv.) was weighed into a 250 ml self-equilibrating dropping funnel and dissolved in ~50 ml of acetonitrile. Hydroxyethyl acrylate (HEA, Aldrich Chemical Co.) (53 g, 0.46 mole) was measured into a 3-neck 2L r.b. flask, fitted with a thermometer (range –100° C.–50° C.), the dropping funnel, a $N_2$ bubbler and a magnetic stirrer. The HEA was dissolved in 700 ml acetonitrile and cooled to 0° C. using a solvent/$CO_2$ bath. Whilst stirring, N,N,N',N'-tetramethylene diamine (TMEDA, Aldrich Chemical Co.) (36 g, 0.24 mol, 1.05 equiv.) were added, followed by the dropwise addition of the CCP solution over a 20 minute period. The reaction mixture went cloudy upon addition of the CCP as the TMEDA.2HCl salt formed. The reaction was left to stir for 2 hours.

The TMEDA.2HCl was filtered off under vacuum and an $N_2$ atmosphere and washed with acetonitrile (~60 ml). The clear pale yellow solution was collected in a 2L Florentine flask. A solvent/$CO_2$ bath was used to cool the solution to ~0° C. before bubbling trimethylamine (TMA, Aldrich Chemical Co.) (81.53, 1.38 mol, 3 equiv.) into the solution, while stirring. The flask was fitted with an air condenser with a balloon attached to the top and stirred at 50° C. for 16 hours. Excess TMA was then removed under vacuum via a solvent/$CO_2$ cold trap, using a HCl trap, whilst stirring at 40° C. ~300 ml of acetonitrile was removed and white solid product of APC was filtered off under vacuum and $N_2$.

Weight of product collected=93.7 g 73%. $^1$H NMR (in $D_2O$) confirmed the product had been made (characteristic singlet for —$N^+(CH_3)_3$@3.15–3.22 ppm, double bond of the acrylate@5.98–6.02 ppm (doublet), 6.19–6.26 ppm (quartet), 6.44–6.48 ppm (doublet)). $^{31}$P NMR (in $CDCl_3$) showed a peak@–0.53 ppm as expected.

EXAMPLE 1

Preparation of the APC:Polyoxyalkyleneamine Adduct 18.73 g (0.067 mol) of APC was weighed into a 100 ml r.b. flask fitted with a condenser and a magnetic stirrer and placed in an oil bath. To this was added 50 ml of IPA and the solution stirred in order to dissolve the solid. A 600 Mw polyoxyalkyleneamine macromonomer (Jeffamine ED600, Huntsman Corp.) (20 g, 0.033 mol) was dissolved in 20 ml of IPA and this was added to the APC solution and the mixture allowed to reflux for 16 hours with stirring. After this time the IPA was removed by vacuum distillation to yield the clear, yellow viscous liquid product. The conversion was almost quantitative (37 g, 97%). $^1$H NMR confirmed the loss of the acrylate double bond, whereas the quaternary ammonium group of the head group could still be clearly seen.

EXAMPLE 2

Preparation of the Polyurethane Urea Based on [1.4 butanediol:Polyoxyalkyleneamine: hexamethylene diisocyanate$_2$]

All glassware was thoroughly dried before use. The Polyoxyalkyleneamine (8.79 g, 22 mmol) was weigh d into an appropriately sized flask equipped with condenser and stirrer, with 40 ml DMSO (Aldrich Chemical Co.) to produce a ~40% w/v. This was stirred at 50° C. until the adduct had dissolved, followed by the addition of two equivalents of hexamethylene diisocyanate (7.39 g, 44 mmol), an appropriate amount of a suitable catalyst (normally 3 drops of stannous octoate) and stirring for 5 minutes to form a prepolymer. The chain extender butanediol (2.00 g, 22 mmol) was then added to the mix and the temperature stirred for 1.5 hours, before raising the temperature to 100° C. for 16 hours. The resulting polymer solution was precipitated into water, and the solid filtered off under vacuum. Residual solvent was removed by Solvent extraction of the solid. The polymer was then dried for at least 24 hours before subjecting to analysis.

Polymer yield=~79%. $^1$H NMR (d$^6$ DMSO) confirmed the polymer structure, peaks for hexamethylene diisocyanate@1.22, 1.32+2.94 ppm, 3.91 ppm (doublet), 3.55 ppm (multiplet), NH of urea@5.60, 5.74+5.84 ppm (singlets), NH of urethane@7.06 ppm (doublet).

FTIR also confirms the structure with absorption peaks for N—H@3339 cm$^{-1}$, C—H@2932 cm$^{-1}$, Urethane —CONH—@1685 cm$^{-1}$, Urea —NHCONH—@1626 cm$^{-1}$, N—H deformation@1561 cm$^{-1}$, C—H@1258 cm$^{-1}$, $CH_2$—O—$CH_2$@1101 cm$^{-1}$.

EXAMPLE 3

Preparation of the Polyurethane Urea Based on [1,4 butanediol: (APC:Polyoxyalkyleneamine): hexamethylene diisocyanate$_2$]

All glassware was thoroughly dried before use. The APC:polyoxyalkyleneamine (7.5 g, 7.8 mmol) and butanediol (0.7 g, 7.8 mmol) was weighed into an appropriately sized flask equipped with mechanical stirrer. This was stirred at 70° C. until the mix became homgenous before cooling to 50° C., followed by the addition of two equivalents of hexamethylene diisocyanate (2.6 g, 15.4 mmol). As the mix thickened to form a stiff white gum 30 ml DMSO (Aldrich Chemical Co.) was added to produce a ~40% w/v solution, which was stirred for a 16 hour period at 50° C. The resulting polymer solution was pr cipitated into 1 l acetone, and the solid filtered off under vacuum. Residual solvent was removed by Soxhlet extraction of the solid. The polymer was then dried for at least 24 hours before subjecting to analysis. Polymer yield=~59%. $^1$H NMR (d$^6$ DMSO) confirmed the polymer structure, peaks for hexamethylene diisocyanate@1.22, 1.37+2.94 ppm, —N$^+$(CH$_3$)$_3$ of PC@3.13 ppm (singlet), 3.92 ppm (doublet), 3.68 ppm (multiplet), NH of urethane@7.05 ppm (doublet).

FTIR also confirms the structure with absorption peaks for N—H@3371 cm$^{-1}$, C—H@2934 cm$^{-1}$, Urethane —CONH—@1718 cm$^{-1}$, Urea —NHCONH—@1631 cm$^{-1}$, N—H deformation@1538 cm$^{-1}$, C—H@1240 cm$^{-1}$, CH$_2$—O—CH$_2$@1089 cm$^{-1}$.

EXAMPLE 4

Preparation of the Polyurethane Urea Based [1,4 butanediol: (APC:Polyoxyalkyleneamine): dicyclohexylmethane diisocyanate$_2$]

All glassware was thoroughly dried before use. The APC:Polyoxyalkyleneamine (7.712 g, 8.0 mmol) and butanediol (0.729, 8.0 mmol) was weighed into an appropriately sized flask equipped with mechanical stirrer. This was stirred at 70° C. until the mix became homgenous before cooling to is 50° C., followed by the addition of two equivalents of dicyclohexylmethane diisocyanate (4.0 g, 15.5 mmol). As the mix thickened to form a stiff white gum 30 ml NMP (Aldrich Chemical Co.) was added to produce a ~40% w/v solution, which was stirred for 16 hours at 50° C. The resulting polymer solution was precipitated into 1 L acetone, and the solid filtered off under vacuum. Residual solvent was removed by Soxhlet extraction of the solid. The polymer was then dried for at least 24 hours before subjecting to analysis.

Polymer yield=~59%. $^1$H NMR (d$^6$ DMSO) confirmed the polymer structure, peaks for dicyclohexylmethane diisocyanate@1.20, 1.44+1.75 ppm (multiplet), —N$^+$(CH$_3$)$_3$ of PC@3.14 ppm (singlet), 3.68 ppm (multiplet), 3.92 ppm (doublet), NH of urea@5.78, 5.90+6.02 ppm (singlets), NH of urethane@7.00 ppm (doublet).

FTIR also confirms the structure with absorption peaks for N—H@3370 cm$^{-1}$, C—H@2971 cm$^{-1}$, Urethane —CONH—@1723 cm$^{-1}$, Urea —NHCONH—@1631 cm$^{-1}$, N—H deformation@1532 cm$^{-1}$, C—H@1234 cm$^{-1}$, CH$_2$—O—CH$_2$@1089 cm$^1$.

EXAMPLE 5

Preparation of the Polyurethane Urea Based on [1.4 butanediol: (APC:Polyoxyalkyleneamine) :diphenylmethane diisocyanate$_2$]

All glassware was thoroughly dried before use. The APC:Polyoxyalkyleneamine (5.5 g, 5.7 mmol) and butanediol (0.51 g, 5.7 mmol) was weighed into an appropriately sized flask equipped with mechanical stirrer. This was stirred at 70° C. until the mix became homgenous before cooling to 50° C., followed by the addition of two equivalents of dicyclohexylmethane diisocyanate (2.85 g, 11.4 mmol). As the mix thickened to form a stiff white gum 30 ml NMP (Aldrich Chemical Co.) was added to produce a ~40% w/v solution, which was stirred for 16 hours at 50° C. The resulting polymer solution was precipitated into 1 L acetone, and the solid filtered off under vacuum. Residual solvent was removed by solvent extraction of the solid. The polymer was then dried for at least 24 hours before subjecting to analysis.

Polymer yield=~59%. $^1$H NMR (d$^6$ DMSO) confirmed the polymer structure, peaks for —N$^+$(CH$_3$)$_3$ of PC@3.12 ppm (singlet), 3.76 ppm (multiplet), 4.05 ppm (doublet), NH of urea@5.55(singlet), NH of urethane@7.03 ppm (doublet), diphenylmethane diisocyanate@7.07+7.35 ppm (doublets).

FTIR also confirms the structure with absorption peaks for N—H@3338 cm$^{-1}$, C—H@2973 cm$^{-1}$, Urethane —CONH—@1729 cm$^{-1}$, Urea —NHCONH—@1651 cm$^{-1}$, N—H deformation@1538 cm$^{-1}$, C—H@1224 cm$^{-1}$, CH$_2$—O—CH$_2$@1089 cm$^{-1}$.

EXAMPLE 6

Properties of Some Selected Polyurethane Ureas Based on [chain extender$_x$: (APC:Polyoxyalkyleneamine): Diisocyanate$_{x+1}$]

The polymers were found to be soluble in 2,2,2-trifluoroethanol. Solutions containing 10 mgml$^{-1}$ were made and used to coat PET strips (9 mm×30 mm) by dipping the strip in and out of the solution at a speed of 3 mmsec$^{-1}$. After air-drying for 16 hours the coated PET strips were subjected to a double antibody fibrinogen assay for the detection of protein adsorption to the strip. Table 1 summarises the results obtained on polymers of the invention as describ d in examples 2–5. The bioevaluation results are expressed as a percentag reduction of the adsorbed protein compared to that adsorbed to an uncoated PET control strip.

Clearly, the inclusion of the PC moiety on the Jeffamine soft s gment leads to a further significant reduction in the amount of fibrinogen that adsorbs to the surface of the coating, compared to the non-PC containing control polyurethane urea. The information from this assay therefore provides further evidence to add to that already in existence, suggesting that the PC group does indeed improve the 'biocompatibility' of the material.

TABLE 1

Preparative and bioevaluation results for some polyurethane ureas.

| Ex. # | Chain Extender | Soft Segment | Diisocyanate | Appearance | Yield (%) | Reduction in Fg (%) |
|---|---|---|---|---|---|---|
| 2 | 1,4-Butanediol (1) | Jeffamine D400 (1) | 1,6-Hexamethylene Diisocyanate (2) | White Solid | 79 | 39 |
| 3 | 1,4-Butanediol (1) | APC:D400 Adduct (1) | 1,6-Hexamethylene Diisocyanate (2) | White Gum | 59 | 72 |
| 4 | 1,4-Butanediol (1) | APC:D400 Adduct (1) | Dicyclohexyl-methane-4,4'-Diisocyanate (2) | White Crystalline Solid | 79 | 66 |
| 5 | 1,4-Butanediol (1) | APC:D400 Adduct (1) | Diphenyl-methane Diisocyanate (2) | White Crystalline Solid | 82 | 83 |

*Numbers in parenthesis indicate molar ratio of the monomer in the polymer.

EXAMPLE 7

Preparation of APC:Aminopropylmethylsiloxane-Dimethylsiloxane Adduct 20 g (0.02 mole NH$_2$) of aminopropylmethylsiloxane-dimethylsiloxane copolymer (APDMS) having an amine equivalent weight of 1000 (AMS-162, Apollo Scientific) was dissolved in 10 g of isopropanol in a suitable flask fitted with a mechanical stirrer, thermometer and $N_2$ feed. A solution of APC (5.6 g, 0.02 mole) dissolved in 16 g isopropanol was added to the APDMS solution and the temperature increased to a set point. The kinetics of this reaction were followed at different temperatures and shown to be complete within 20, 40 & 80 minutes at 80, 60 & 40° C. respectively. 60° C. was chosen as the preferred reaction temperature to reduce the possibility of acrylate homopolymerisation. After 60 minutes at 60° C. the product was evaporated to dryness using a rotary evaporator to give 26 g of a viscous gum. $^1$H NMR confirmed the loss of the HEA acrylate double bond (5.8(d)/6.1(q)16.4(d)).

Peak assignments (Jeol GSX 400, 399.9 MHz, $CDCl_3$, ppm): ~0.1 (Si—$CH_3$); 0.45 (Si—$CH_2$—); 1.50 (Si—$CH_2$—$CH_2$—); 2.55 (combined multiplet, —$CH_2$—NH—$CH_2$—); 2.87 (—$CH_2$—CO—); 3.71 (—$CH_2$—OH); 4.22 (—COO—$CH_2$—)

EXAMPLE 8a

Preparation of Allyl Isocyanate Adduct of Example 7

The adduct from Example 7 (23 g) was dissolved in THF (90 g) in a suitable flask fitted with a mechanical stirrer, thermometer and $N_2$ feed. The flask and contents were heated to 45° C. to aid dissolution. A solution of allyl isocyanate (1.5 g) in THF (3.0 g) was quickly added. A small exotherm was observed and the temperature was then raised to 60° C. and held for 1 hour. FT-IR spectroscopy of the liquor after this time showed no characteristic peak for the isocyanate stretch at ~2259 $cm^{-1}$. The solvent was evaporated to give a very viscous gum. $^1$H NMR (in $CD_3OD$) confirmed that the product was the desired allyl derivative:

(Jeol GSX 400, 399.9 MHz, $CDCl_3$, ppm): ~0.1 (Si—$CH_3$); 0.46 (Si—$CH_2$—); 1.57 (Si—$CH_2$—$CH_2$—); 2.59 ($CH_2$—COO—); 3.08 (b, $CH_2$—N—$CH_2$ & CONH—$CH_2$—); 3.30 ($N^+(CH_3)_3$); 3.49/3.8/4.1/4.25 (—$COOCH_2CH_2OP(OO—)OCH_2CH_2$—N—); 4.22 (—COO—$CH_2$—); 5.05/5.15/5.87 (allyl-CH=$CH_2$)

EXAMPLE 8b

Preparation of a Silicone/APC/Al Macromer 7.4 g of APC was weighed into a 250 ml r.b. flask fitted with stirrer, thermometer and nitrogen blanket. 18.0 g of iPA solvent was added and the mixture was heated to 60° C. The APC completely dissolved at about 50° C. 30 g of AMS 162 was added with a wash of a further 7.0 g of iPA The temperature was held at 60° C. for 15 min and then raised to reflux (ca. 80° C.). After 1 h the reaction was cooled to 40° C. and 2.1 g of allyl isocyanate (Al) (Aldrich) added with a wash of 1.4 g of iPA. An exotherm was noted and the mixtur was heated to reflux for 1 h. After cooling, FT-IR spectroscopy confirmed the reaction of all isocyanate by loss of the N=C=O stretch.

Removal of the solvent under vacuum to yield a thick gum and subsequent $^1$H NMR analysis of this product confirmed the expected structure for the adduct.

EXAMPLE 9

Preparation of APC-Polydimethylsiloxane Using an Amine-Functional PDMS, APC and an Unsaturated Isocyanate 11.2 g of APC (0.04 mole) and hydroxyethyl methacrylate (30.5 g) were charged into a flask fitted with a thermometer, mechanical stirrer and $N_2$ blanket The contents were stirred at room temperature until a clear solution was obtained. Hydroquinone (ca. 0.001 g) was added (to inhibit the premature polymerisation of the hydroxyethyl methacrylate) followed by 40 g (0.04 mole) of aminopropylmethylsiloxane-dimethylsiloxane copolymer. The temperature was raised to 60° C. and after about 20 minutes the solution cleared. The reaction was maintained at 60° C. for 1 hour. The reaction was then cooled to 30° C. and 8.0 g (0.04 mole) of dimethyl meta-isopropenyl benzyl isocyanate (m-TMI, Cytec Industries) added with good stirring. This reacts selectively with the secondary amine and not the alcohol group of the hydroxyethyl methacrylate. A small exotherm was observed and the temperature was then raised to 55° C. and held for 1 hour. The product was obtained as a 67% solution in hydroxyethyl methacrylate.

EXAMPLES 10–18

The Preparation of an APC-Polydimethylsiloxane Adducts Suitable for Use in Contact Lens Formulations Using a synthetic procedure based on that described for Example 9, macromers suitable for use in contact lens manufacture were made using the components described in Table 2:

TABLE 2

APC-Silicone macromers for contact lens formulation

| Example # | Silicone | Other Amine | Iso-cyanate | Cap | Adductor | Solvent |
|---|---|---|---|---|---|---|
| 10 | AMS-162 | — | TMI | — | APC | IPA |
| 11 | AMS-162 | — | TMI | — | APC | DMA |
| 12 | AMS-162 | — | TMI | — | APC | IPA/Hex |
| 13 | DMS-A12 | — | TMXDI | BAM | APC | IPA |
| 14 | DMS-A12 | — | HMDI | HEMA | APC | Hexanol |
| 15 | DMS-A15 | — | TMI | — | APC | HEMA |
| 16 | DMS-A15 | JED600 | TMXDI | BAM | APC | IPA |
| 17 | DMS-A15 | ED | TMXDI | BAM | APC | IPA/Hex |
| 18 | DMS-A15 | JED600 | TMXDI | TMI | APC | IPA |

The term "Cap" is used to denote the group which "endaps" to product. The usual order of reaction is the Michael addition followed by addition of a cap and then a diisocyanate to extend the chain. The term "other amine" is used to denote any diamine for which the ratio of diisocyanate is adjusted such that some chain extension is achieved using the "other amine" before capping is carried out.

EXAMPLE 19

Generic Method for Contact Lens Preparation and Evaluation

The contact lens formulation (macromer/comonomers/initiator/crosslinker) was placed into a glass vial and the mixture degasssed for 10 mins with $N_2$ before dispensing known amounts into polypropylene contact lens moulds (to give −3.0 D power lenses). The moulds were then sealed and UV cured for 1 hour using a Blak-Ray longwave UV lamp model B100AP. The lenses were removed from the mould by soaking in high purity water for 1 hour. They were then soaked in a 70:30 water IPA solution for 2 hours and in borate buffered saline for a further hour. The lenses were then bottled in buffer. A visual assessment of the lenses was made and this was recorded.

Lenses were placed in vials that were filled with buffer solution. They wer then sterilised by autoclaving at 120° C. for 30 mins. A visual assessment of the lenses was made and this was recorded.

Th equilibrium water content (EWC) of the lens was determined by firstly removing excess (free) water from the lens surface by use of filter paper. The lenses were then placed on a Pyrex dish containing drierite and microwaved for 5 minutes on full power (800 watts) and reweighed. The EWC was then calculated as follows:

$$EWC\ (\%) = \frac{\text{hydrated weight of lens} - \text{dry weight of lens}}{\text{hydrated weight of lens}} \times 100\%$$

The oxygen permeability (Dk) of the lenses was determined by use of Mocon's OptiPerm™ technology according to their SOP#70-006, designed for measuring the Dk value of hydrophilic contact lens materials (Mocon/Modem Controls Inc., 7500 Boone Avenue North, Minneapolis, Minn., 55428 USA). In the cases where the Michael-type adduct is prepared using hydroxyethyl methacrylate as a solvent, this is usually to avoid using a solvent in the formation of contact lenses. This allows direct formulation into hydroxyethyl methacrylate-based lenses and the hydroxyethyl methacrylate is not recovered from the Michael reaction.

EXAMPLES 20–23

The Preparation of a Moulded Contact Lenses Using Selected Adducts from Examples 9–18

TABLE 3

Lens formulations using macromers of the invention.

| Example # | Macromer Example # | Macromer (g) | NNDMA (g) | TRIS (g) | EGDMA (g) | Darocur (g) |
|---|---|---|---|---|---|---|
| 20 | 9 | 1.2438 | 0.7069 | 0.6575 | — | 0.0230 |
| 21 | 12 | 1.2523 | 0.6604 | 0.6336 | 0.025 | 0.025 |
| 22 | 13 | 1.8291 | 0.7503 | 0.5773 | 0.0532 | 0.0311 |
| 23 | 16 | 1.5841 | 0.2610 | 0.7794 | 0.0557 | 0.025 |

Typical examples of the properties of the lenses formed are shown in Table 4 below. Lenses were clear upon hydration and could be made with a wide range of EWCs. Oxygen p rmeability could be altered by formulating with more silicone content.

TABLE 4

Properties of lenses made using macromers of the invention.

| Example # | Appearance (p st UV cure) | EWC (%) | Dk × 10$^{10}$ (ccO$_2$/cm$^2$ sec mmHg) |
|---|---|---|---|
| 20 | Clear, colourless | 24.7 | * |
| 21 | Clear, colourless | 18.4 | * |
| 22 | Clear, colourless | 31.0 | 81.9 |
| 23 | Clear, colourless | 11.3 | * |

(* = Not tested for Dk)

Biological properties of lenses made from the invention were also favourable compared to commercially available hydrogel and silicone hydrogel lenses. Lenses were assessed using a UV detection method at 280 nm (Table 5):

TABLE 5

Total protein adsorption to various lens types.

| Example # | Lens Type | Total Protein Adsorption (mg protein/lens) | Ewc (%) | (ccO$_2$/cm$^2$sec mmHg) D$_k$ + 10$^{10}$ |
|---|---|---|---|---|
| Omafilcon A | Hydrogel | 9.37 ± 1.94 | 62 | 27 |
| Balafilcon A | Silicone Hydrogel | 11.35 ± 2.59 | 36 | 99 |
| 22 | Invention | 5.28 ± 2.00 | 31 | 81.9 |

EXAMPLE 24

Preparation of an APC-Trimethoxysilane Based Adduct as a Coating Formulation 11 g (0.039 mol) of APC were dissolved in 50 ml IPA with gentle warming and stirring under an atmosphere of N$_2$. Once clear, 6.80 g (0.039 mol) of 3-aminopropyl trimethoxysilane (3-APTMS) were added and the reaction mixture bought to reflux for 1 hour. $^1$H & $^{13}$C NMR showed conversion to the Michael adduct and proton COSY was used to assign the peaks.

$^1$H NMR (CDCl$_3$, 400 MHz, ppm): 0.61 (2H, m, Si—CH$_2$—), 1.20 (d, exchanged iPA —CH$_3$), 1.60 (2H, m, Si—CH$_2$—CH$_2$—), 2.55 (2H, t, CH$_2$—COO—), 2.60 & 2.88 (2H each, t, CH$_2$—NH—CH$_2$), 3.42 (9H, s, N$^+$(CH$_3$)$_3$), 3.52 (integral shows some exchange with iPA has occurred, CH$_3$—O—Si), 3.80 (2H, b, CH$_2$—N$^+$(CH$_3$)$_3$), 4.10 (2H, b, COO—CH$_2$CH$_2$—O—P), 4.21, (m, exchanged iPA (m, —CHOH), 4.24 (2H, b, COO—CH$_2$—), 4.29 (2H, b, P—O—CH$_2$—CH$_2$—N$^+$(CH$_3$)$_3$). $^{13}$C NMR (CDCl$_3$) further supports assignment of structure with characteristic peaks, e.g. 172 (C=O), 54.9 (N$^+$(H$_3$)$_3$).

FT-IR indicates carbonyl/ester, Si—O—CH$_3$ and Si—O—CH(CH$_3$)$_2$ present.

To the cooled IPA solution was added 3.29 g of hexamethylene diisocyanate (0.0196 mol) and the reaction mixture taken to reflux for a further hour. FT-IR confirmed reaction of the isocyanate by disappearance of the N=C=O stretch at ~2230 cm$^{-1}$. $^1$H NMR & $^{13}$C confirmed formation of the APC-TMS dimer.

$^1$H NMR (CDCl$_3$, 400 MHz, ppm): 0.55 (2H, m, Si—CH$_2$—), 1.20 (d, exchanged iPA —CH$_3$), 1.30 (2H, b, CH$_2$—CH$_2$—CH$_2$—NHCO), 1.48 (2H, b, CH$_2$—CH$_2$—NHCO), 1.62 (2H, m, Si—CH$_2$—CH$_2$—), 2.57 (2H t, CH$_2$—COO—), 3.12 (4H, b, CH$_2$NH—CH$_2$), 3.42 (9H, s, N$^+$(CH$_3$)$_3$), 3.48 (2H, b, CH$_2$—NHCO), 3.52 (integral shows some exchange with iPA has occurred, CH$_3$—O—Si), 3.80 (2H, b, CH$_2$—N$^+$(CH$_3$)$_3$), 4.05 (2H, b, COO—CH$_2$—CH$_2$—O—P), 4.21, (m, exchanged iPA (m, —CHOH), 4.24 (2H, b, COO—CH$_2$—), 4.29 (2H, b, P—O—CH$_2$—CH$_2$—N$^+$(CH$_3$)$_3$). $^{13}$C NMR (CDCl$_3$) further supports assignment of structure with characteristic peaks, e.g. 172 (C=O), 154 (—NRCONH—), 54.9 (N$^+$(CH$_3$)$_3$), 26, 30 & 41 (dimer bridging methylene groups)

EXAMPLE 25

Biological Evaluation of a Coating Based on Example 24

A solution of 20 mgml$^{-1}$ of the APC-trimethoxysilane compound described in example 24 in iPA was coated onto PET at a speed of 3 mmsec$^{-1}$. The PET strip was allowed to air dry for 30 minutes before the coating was cured in an oven at 70° C. overnight. The coated PET samples were assessed for their ability to resist adsorption of protein using an enzyme immunoassay based on fibrinogen. The data shown in Table 6 shows that the coating substantially reduced the amount of fibrinogen that adsorbed to the surface compared to the uncoated control.

TABLE 6

Reduction of fibrinogen adsorption for coatings of Example 24.

| Sample Type | Absorbance @ 450 nm (n = 7) | Standard Deviation | % Reduction of Fg Adsorption |
|---|---|---|---|
| Uncoated PET | 1.795 | 0.350 | N/A |
| PET coated as per example 15 | 0.551 | 0.090 | 69.3 |

A similar enzyme immunoassay that shows the extent of bacterial adhesion (*E. coli*) to substrates was used to challenge PET samples coated with the invention of Example 24. The data shows substantial reduction of bacterial adhesion to the surface of the coated sample relative to the control.

TABLE 7

Reduction of *E. Coli* adhesion for coatings of Example 24.

| Sample Type | Absorbance @ 450 nm (n = 5) | Standard Deviation | % Reduction f E. Coli Adhesion |
|---|---|---|---|
| Uncoated PET | 0.639 | 0.071 | N/A |
| PET coated as per example 15 | 0.149 | 0.021 | 76.8 |

EXAMPLE 26

The Preparation of APC-Surfactants 9.2 g (0.05 mol) of dodecylamine was dissolved in 9.2 g of isopropanol in a 3-neck flask fitted with a thermometer, mechanical stirrer and $N_2$ blanket Separately, 14.0 g of APC (005 mol) was dissolved in 28 g of isopropanol with warming and the solution added to the amine solution. The temperature of the reaction mixture was raised to reflux (83° C.) and held for 4 hours. After this time the solvent was evaporated under vacuum and the product obtained as a waxy solid. The structure was confirmed by $^1H$ (given) and $^{13}C$ NMR.

$^1$HNMR ($CD_3OD$, ppm, 400 MHz): 0.9 (triplet, 3H, terminal $CH_3$ on alkyl chain); 1.3–1.6 (broad, 20H, alkyl chain —$CH_2$—); 2.5–2.7 (multiplet, 4H, —$CH_2$—NH—$CH_2$—); 2.9 (triplet, 2H, —$CH_2$—CO—); 3.3 (sharp singlet, 9H, $N^+(CH_3)_3$); 3.7–4.4 (deshielded —$CH_2$— from APC bridging methylene groups.

12 g of this product were dissolved in 46 g of THF at 40° C. A solution of 2.0 g allyl isocyanate (Aldrich) in 2 g of THF was added. A small exotherm was observed and the temperature of the reaction was raised to reflux and held for 1 hour. After this time 10 g of ethanol was added and refluxing continued for a further 1 hour. After this time the solvents were evaporated under vacuum to give 14.6 g of a waxy solid. The structure was confirmed by $^1H$ and $^{13}C$ NMR.

$^1$H NMR ($CD_3OD$, 400 MHz) confirms allyl group present (characteristic ABC splitting, multiplet at 5.75; doublet of doublets 4.95% 5.15). $^{13}C$ NMR corroborates allyl group (115.0 & 137.5), urea linkage (159.6) and ester carbonyl (173.4).

What is claimed is:

1. A zwitterion containing adduct having the formula (I)

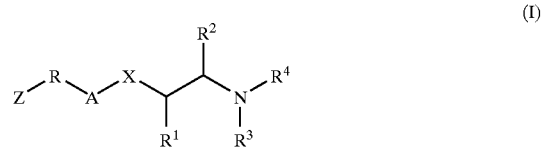

wherein

Z is a zwitterionic group with a general formula (IV)

in which the moieties $A^2$ and $A^3$, which are the same or different, are —O—, —S—, —NH— or a valence bond $W^+$ is a group of formula —$W^1$—$N^+R^{14}_3$, —$W^1$—$P^+R^{15}_3$, —$W^1$—$S^+R^{15}_2$ or —$W^1$—$Het^+$ in which:

$W^1$ is alkanediyl of 1 or more carbon atoms optionally containing one or more ethylenically unsaturated double or triple bonds, disubstituted-aryl (arylene), alkylene arylene, arylene alkylene, or alkylene aryl alkylene, cycloalkanediyl, alkylene cycloalkyl, cycloalkyl alkylene or alkylene cycloalkyl alkylene, which group $W^1$ optionally contains one or more fluorine substituents and/or one or more functional groups; and either the groups $R^{14}$ are the same or different and each is hydrogen or alkyl of 1 to 4 carbon atoms, or two of the groups $R^{14}$ together with the hetero atom to which they are attached form an aliphatic heterocyclic ring containing from 5 to 7 atoms, or the three groups $R^{14}$ together with the hetero atom to which they are attached form a fused ring structure containing from 5 to 7 atoms in each ring, and optionally one or more of the groups $R^{14}$ is substituted by a hydrophilic functional group, and the groups $R^{15}$ are the same or different and each is $R^{14}$ or a group $OR^{14}$, where $R^{14}$ is as defined above; or Het is an aromatic nitrogen-, phosphorus- or sulphur-containing ring;

X is an electron withdrawing group selected from the group consisting of carbonyl and sulphone groups, sulphonium and phosphonium salts;

R is selected from the group consisting of linear and branched alkanediyl, alkenediyl, alkynediyl, cycloalkanediyl, cycloalkenediyl, cycloalkynediyl, arylene, alkarylene, aralkylene, alkoxyarylene, alkoxyalkyl, oligo(alkoxy)alkyl, mono- and di-alkylaminoalkyl N-arylaminoalkyl, N-aryl-N-alkylaminoalkyl; $R^1$ and $R^2$ are independently selected from hydrogen and $C_1$–$C_{12}$ alkyl groups; A is O or $NR^6$, where $R^6$ is selected from the group consisting of hydrogen and $C_{1-6}$ alkyl;

$R^3$ is selected from the group consisting hydrogen, linear and branched alkyl, alkenyl, and alkynyl groups, alkoxycarbonyl, alkylaminocarbonyl, cycloalkyl, cycloalkenyl, cycloalkynyl, haloaryl, haloalkyl, aryl, alkaryl, aralkyl, alkoxyaryl, alkoxyalkyl, oligoalkoxyalkyl, aminoalkyl, mono- and di-alkylaminoalkyl, arylaminoalkyl, N-aryl-N-alkylaminoalkyl and -aminoaryl, acyloxy, acyloxyalkyl, acylaminoalkyl, N-diacyl-iminoalkyl groups, mono- and di-alkylaminocarbonyl, organosilyl, arylamino carbonyl, aryl(alkyl)amino carbonyl, and organosiloxyl groups and any of the above groups substituted with a reactive group, a group $NHCOOR^5$ in which $R^5$ is selected from the group consisting hydrogen, linear and branched alkyl, alkenyl, and alkynyl groups, cycloalkyl, cycloalkenyl, cyctoalkynyl, haloaryl, haloalkyl, aryl, alkaryl, aralkyl, alkoxyaryl, alkoxyalkyl, oligoalkoxyalkyl, aminoalkyl, mono- and di-alkylaminoalkyl, arylaminoalkyl, N-aryl-N-alkylaminoalkyl and aminoaryl, acyloxyalkyl, acylaminoalkyl, N-diacyl-iminoalkyl groups, hydroxyalkyl, hydroxyalkenyl, hydroxyalkynyl, hydroxyaryl, hydroxyalkoxyalkyl and hydroxy (oligoalkoxy)alkyl;

a group $-NHCONR^7R^8$ in which $R^7$ and $R^8$ are selected from the group consisting hydrogen, linear and branched alkyl, alkenyl, and alkynyl groups, cycloalkyl, cycioalkenyl, cycloalkynyl, haloaryl, haloalkyl, aryl, alkaryl, aralkyl, alkoxyaryl, alkoxyalkyl, oligoalkoxyalkyl, aminoalkyl, mono- and dialkylaminoalkyl, arylaminoalkyl, N-aryl-N-alkylaminoalkyl and aminoaryl, acyloxyalkyl, acylaminoalkyl, N-diacyl-iminoalkyl groups, hydroxyalkyl, hydroxyalkenyl, hydroxyalkynyl, hydroxyaryl, hydroxyalkoxyalkyl and hydroxy (oligoalkoxy)alkyl; or a polymeric moiety; and $R^4$ is selected from the group consisting hydrogen, linear and branched alkyl, alkenyl, and alkynyl groups, alkoxycarbonyl, alkylaminocarbonyl, cycloalkyl, cycloalkenyl, cycloalkynyl, haloaryl, haloalkyl, aryl, alkaryl, aralkyl, alkoxyaryl, alkoxyalkyl, oligoalkoxyalkyl, aminoalkyl, mono- and di-alkylaminoalkyl, arylaminoalkyl, N-aryl-N-alkylaminoalkyl and -aminoaryl, acyloxy, acyloxyalkyl, acylaminoalkyl, N-diacyl-iminoalkyl groups, mono- and di-alkylaminocarbonyl, organosilyl, arylamino carbonyl, aryl(alkyl)amino carbonyl, and organosiloxyl groups and any of the above groups substituted with a group II

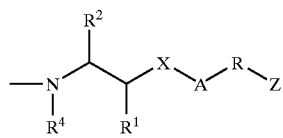

(II)

in which the groups R, $R^1$, $R^2$, $R^4$, Z and A are the same as in (I);

a group III

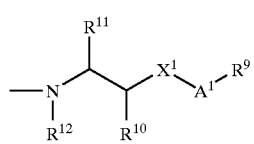

(III)

in which $A^1$ is O or $NR^{13}$ where $R^{13}$ is hydrogen or $C_{1-6}$ alkyl;

$X^1$ is an electron withdrawing group selected from carbonyl, sulphonyl, sulphonium and phosphonium groups;

$R^{12}$ is H or $C_{1-6}$ alkyl;

$R^{10}$ and $R^{11}$ are independently selected from H and $C_{1-4}$ alkyl; and $R^9$ is optionally substituted alkyl or aryl;

a reactive group; or a polymeric moiety.

2. An adduct according to claim 1, wherein $W^+$ is $W^1N^+R^{14}_3$, wherein $W^1$ is a $C_{1-12}$ alkanediyl group.

3. An adduct according to claim 1 or 2 wherein the zwitterionic group of the formula (IV), has the general formula (V):

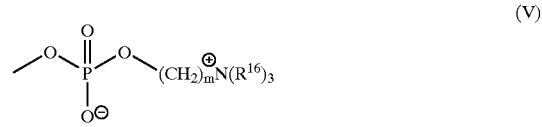

(V)

where the groups $R^{16}$ are the same or different and each is hydrogen or $C_{1-4}$ alkyl, and m is from 1 to 4.

4. An adduct according to claim 1, wherein X is a carbonyl group.

5. An adduct according to claim 1, wherein A is 0.

6. An adduct according to claim 1, wherein $R^1$ and $R^2$ are independently selected from the group consisting of hydrogen and $C_{1-4}$ alkyl.

7. An adduct according to claim 1 in which $R^3$ is hydrogen.

8. An adduct according to claim 1 in which $R^3$ is an optionally substituted alkyl- or aryl-aminocarbonyl.

9. An adduct according to claim 1, wherein $R^3$ comprises a reactive group capable of forming a covalent bond to a polymer, to a monomer bearing a site of unsaturation, or to a substrate.

10. An adduct according to claim 9, wherein the reactive group is isocyanate, allyl, isopropenyl or (meth)acryloyloxy.

11. An adduct according to claim 1, wherein $R^4$ is an organosiloxyl group having a formula weight in the range 300 to 20000 D and having the formula (IX)

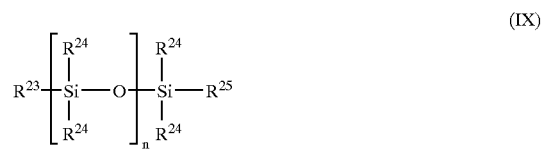

(IX)

in which at least one of the grups $R^{23}$, $R^{24}$ and $R^{25}$ is a divalent moiety selected from the group consisting of a valence bond, $C_{1-12}$ alkanediyl, $C_{2-12}$ alkenediyl and $C_{2-12}$ alkynedlyl and is covalently bonded to the nitrogen atom of adduct (I) and the remaining groups $R^{23}$, $R^{24}$ and $R^{25}$ each represent a monovalent moiety independently selected from the group consisting of branched and straight $C_{1-12}$ alkyl, $C_{6-18}$ aryl, $C_{6-18}$ alkaryl, $C_{6-18}$ aralkyl, $C_{2-12}$ alkenyl and $C_{2-12}$ alkynyl any of which may be substituted by a primary, secondary, tertiary amine group or by a group III as defined in claim 1; and n is 0–300.

12. An adduct according to claim 11, wherein $R^{23}$ and $R^{25}$ are selected from methanediyl, ethanediyl, propanediyl and butanediyl, and are both covalently bound to the nitrogen atom of individual adducts (I).

13. An adduct according to claim 11 or claim 12, wherein the groups $R^{24}$ are independently selected from the group consisting of $C_{1-6}$ alkyl groups, $C_{1-4}$ alkyl groups.

14. A zwitterion containing adduct having the formula (X), (XI), or (XIII)

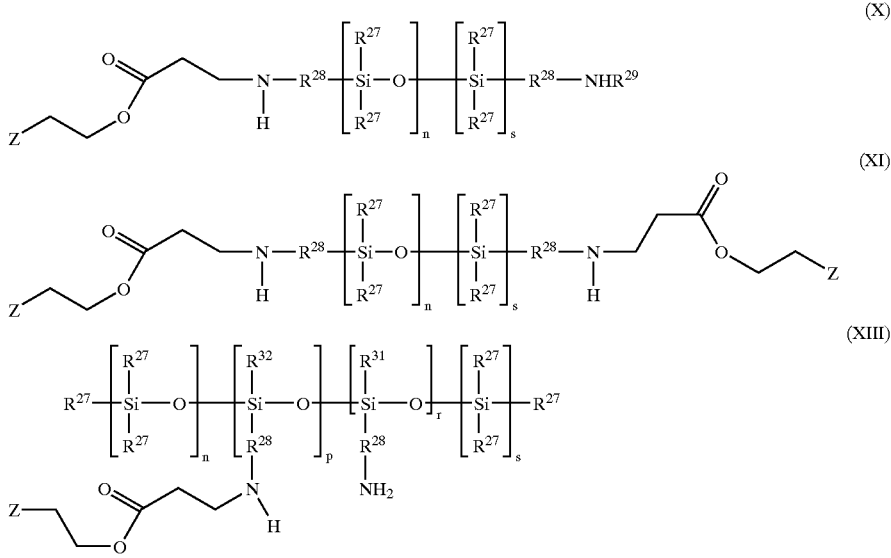

wherein
- Z is a zwitterionic group;
- wherein each of the groups $R^{27}$ is independently selected from the group consisting of $C_{1-6}$ alkyl, $C_{6-18}$ aryl, $C_{6-18}$ aralkyl, $C_{6-8}$ alkaryl, $C_{2-6}$ alkenyl;
- each $R^{28}$ is independently selected from the group consisting of $C_{1-6}$ alkanediyl, $C_{2-6}$ alkendiyl and $C_{2-6}$ alkynediyl;
- $R^{31}$ is selected from the same groups as $R^{27}$ or is a group $R^{28}$ $NH_2$;
- $R^{32}$ is selected from the same groups as $R^{27}$ or is a group $R^{28}$ $NH_2$ or a group $R^{28}$ $NH(CH_2)_2COO(CH_2)_2$ Z or a group —$R^{28}N(CONHR^{30})CH_2CH_2COO(CH_2)_2Z$;
- $R^{29}$ is selected from the group consisting of hydrogen, $C_{1-6}$ alkyl, $C_{6-18}$ aryl, $C_{6-18}$ aralkyl, $C_{2-6}$ alkenyl, $C_{6-18}$ alkaryl;
- n is an integer of 1 to 500;
- p is an integer of 1 to 50;
- q is an integer of 1 to 500;
- r is an integer of 1 to 50; and
- s is 0 to 1.

15. An adduct according to claim 14, wherein all groups $R^{27}$, $R^{31}$ and $R^{32}$ are methyl and $R^{28}$ is selected from ethanediyl, propanediyl and butanediyl.

16. A zwitterion containing adduct having the formula (I)

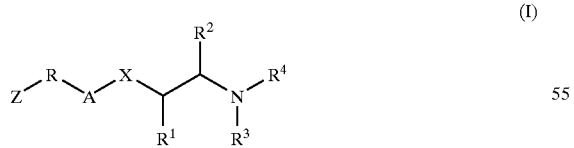

wherein
- Z is a zwitterionic group;
- X is an electron withdrawing group selected from the group consisting of carbonyl and sulphone groups, sulphonium and phosphonium salts;
- R is selected from the group consisting of linear and branched alkanediyl, alkenediyl, alkynediyl, cycloalkanediyl, cycloalkenediyl, cycloalkynediyl, arylene, alkarylene, aralkylene, alkoxyarylene, alkoxyalkyl, oligo(alkoxy)alkyl, mono- and di-alkylaminoalkyl N-arylaminoalkyl, N-aryl-N-alkylaminoalkyl; $R^1$ and $R^2$ are independently selected from hydrogen and $C_1-C_{12}$ alkyl groups; A is O or $NR^6$, where $R^6$ is selected from the group consisting of hydrogen and $C_{1-4}$ alkyl;
- $R^3$ is selected from the group consisting hydrogen, linear and branched alkyl, alkenyl, and alkynyl groups, alkoxycarbonyl, alkylaminocarbonyl, cycloalkyl, cycloalkenyl, cycloalkynyl, haloaryl, haloalkyl, aryl, alkaryl, aralkyl, alkoxyaryl, alkoxyalkyl, oligoalkoxyalkyl, aminoalkyl, mono- and di-alkylaminoalkyl, arylaminoalkyl, N-aryl-N-alkylaminoalkyl and -aminoaryl, acyloxy, acyloxyalkyl, acylaminoalkyl, N-diacyl-iminoalkyl groups, mono- and di-alkylaminocarbonyl, organosilyl, arylamino carbonyl, aryl(alkyl)amino carbonyl, and organosiloxyl groups and any of the above groups substituted with
- a reactive group,
- a group $NHCOOR^5$ in which $R^5$ is selected from the group consisting hydrogen, linear and branched alkyl, alkenyl, and alkynyl groups, cycloalkyl, cycloalkenyl, cycloalkynyl, haloaryl, haloalkyl, aryl, alkaryl, aralkyl, alkoxyaryl, alkoxyalkyl, oligoalkoxyalkyl, aminoalkyl, mono- and di-alkylaminoalkyl, arylaminoalkyl, N-aryl-N-alkylaminoalkyl and aminoaryl, acyloxyalkyl, acylaminoalkyl, N-diacyl-iminoalkyl groups, hydroxyalkyl, hydroxyalkenyl, hydroxyalkynyl, hydroxyaryl, hydroxyalkoxyalkyl and hydroxy (oligoalkoxy)alkyl;
- a group —$NHCONR^7R^8$ in which $R^7$ and $R^8$ are selected from the group consisting hydrogen, linear and branched alkyl, alkenyl, and alkynyl groups, cycloalkyl, cycioalkenyl, cycloalkynyl, haloaryl, haloalkyl, aryl, alkaryl, aralkyl, alkoxyaryl, alkoxyalkyl, oligoalkoxyalkyl, aminoalkyl, mono- and dialkylaminoalkyl, arylaminoalkyl, N-aryl-N-alkylaminoalkyl and aminoaryl, acyloxyalkyl, acylaminoalkyl, N-diacyl-iminoalkyl groups, hydroxyalkyl, hydroxyalkenyl, hydroxyalkynyl, hydroxyaryl, hydroxyalkoxyalkyl and hydroxy (oligoalkoxy)alkyl; or
- a polymeric moiety; and $R^4$ is the group of the formula (XV)

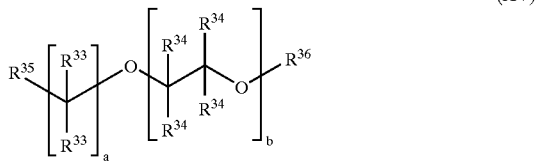
(XV)

wherein each group $R^{33}$ is independently selected from the group consisting of hydrogen, $C_{1-6}$ alkyl, $C_{6-18}$ aryl, $C_{6-18}$ aralkyl, $C_{6-18}$ alkaryl and $C_{2-6}$ alkenyl; each group $R^{34}$ is independently selected from the group consisting of hydrogen, $C_{1-6}$ alkyl, $C_{6-18}$ aryl, $C_{6-18}$ aralkyl, $C_{6-18}$ alkaryl and $C_{2-6}$ alkenyl;

$R^{35}$ is a divalent moiety selected from the group consisting of a valence bond, $C_{1-6}$ alkanediyl, $C_{6-18}$ arylene, $C_{6-18}$ aralkylene, $C_{2-6}$ alkenediyl, mono-, di- and tri-alkylaminoalkyl, arylaminoalkyl, arylaminoaryl, N-aryl-N-alkylaminoalkyl and -aminoaryl;

$R^{36}$ is a divalent moiety selected from the same groups as $R^{35}$ or is a monovalent moiety selected from the same groups as $R^{33}$, aminoalkyl and aminoaryl, and alkyl and aryl groups substituted by groups of general formula II or III as defined in claim 1;

a is 0 or an integer in the range of 1–10, b is 0 or an integer of in the range 1–500; and (XV) has a formula weight of 100–10000.

17. An adduct according to claim 16, wherein the adduct has the formula (XVI), (XVII) or (XVII)

each group $R^{34}$ is independently selected from the group consisting of hydrogen, $C_{1-4}$ alkyl, $C_{6-18}$ aryl, $C_{6-18}$ aralkyl, and $C_{6-18}$ alkaryl;

c is 0 or an integer in the range 1 to 10;

$R^{38}$ is selected from the group consisting of hydrogen $C_{1-4}$ alkyl, $C_{6-18}$ aryl, $C_{6-18}$ aralkyl, $C_{6-18}$ alkaryl, and $C_{2-6}$ alkenyl; and each $R^{39}$ is independently selected from the group consisting of hydrogen, linear and branched alkyl, alkenyl, and alkynyl groups, alkoxycarbonyl, alkylaminocarbonyl, cycloalkyl, cycloalkenyl, cycloalkynyl, haloaryl, haloalkyl, aryl, alkaryl, aralkyl, alkoxyaryl, alkoxyalkyl, oligoalkoxyalkyl, aminoalkyl, mono-, di- and tri-alkylaminoalkyl, arylaminoalkyl, N-aryl-N-alkylaminoalkyl and -aminoaryl, acyloxy (including alkenoyloxy), acyloxyalkyl (including alkenoloxyalkyl), acylaminoalkyl, N-diacyliminoalkyl groups, alkylaminocarbonyl, organosilyl and organosiloxyl groups and any of the above groups substituted with a zwitterionic group Z or an isocyanate group.

18. A zwitterion containing adduct having the formula (I)

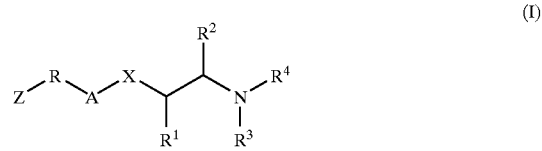
(I)

wherein

Z is a zwitterionic group;

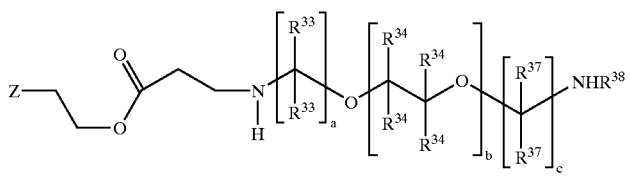
(XVI)

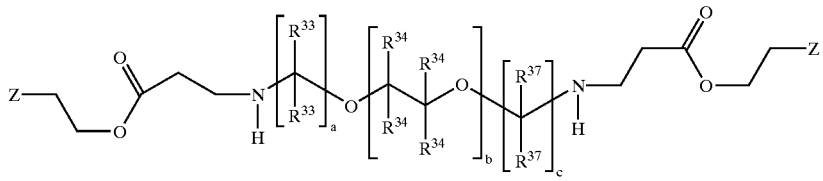
(XVII)

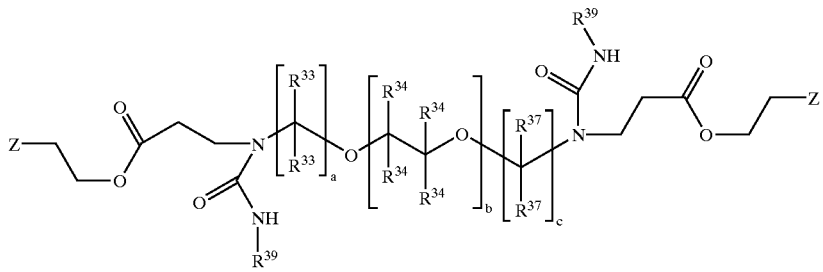
(XVIII)

wherein each group $R^{33}$ is independently selected from the group consisting of hydrogen, $C_{1-4}$ alkyl, $C_{6-18}$ aryl, $C_{6-18}$ aralkyl, and $C_{6-18}$ alkaryl;

each group $R^{37}$ is independently selected from the group consisting of hydrogen, $C_{1-4}$ alkyl, $C_{6-18}$ aryl, $C_{6-18}$ aralkyl, and $C_{6-18}$ alkaryl;

X is an electron withdrawing group selected from the group consisting of carbonyl and sulphone groups, sulphonium and phosphonium salts;

R is selected from the group consisting of linear and branched alkanediyl, alkenediyl, alkynediyl, cycloalkanediyl, cycloalkenediyl, cycloalkynediyl, arylene, alkarylene, aralkylene, alkoxyarylene, alkoxyalkyl, oligo(alkoxy)alkyl, mono- and di-alkylaminoalkyl N-arylaminoalkyl, N-aryl-N-alkylaminoalkyl; $R^1$ and $R^2$ are independently selected from hydrogen and $C_1$–$C_{12}$ alkyl groups; A is O or $NR^6$, where $R^6$ is selected from the group consisting of hydrogen and $C_{1-6}$ alkyl;

$R^3$ is selected from the group consisting hydrogen, linear and branched alkyl, alkenyl, and alkynyl groups, alkoxycarbonyl, alkylaminocarbonyl, cycloalkyl, cycloalkenyl, cycloalkynyl, haloaryl, haloalkyl, aryl, alkaryl, aralkyl, alkoxyaryl, alkoxyalkyl, oligoalkoxyalkyl, aminoalkyl, mono- and di-alkylaminoalkyl, arylaminoalkyl, N-aryl-N-alkylaminoalkyl and -aminoaryl, acyloxy, acyloxyalkyl, acylaminoalkyl, N-diacyl-iminoalkyl groups, mono- and di-alkylaminocarbonyl, organosilyl, arylamino carbonyl, aryl(alkyl)amino carbonyl, and organosiloxyl groups and any of the above groups substituted with a reactive group, a group $NHCOOR^5$ in which $R^5$ is selected from the group consisting hydrogen, linear and branched alkyl, alkenyl, and alkynyl groups, cycloalkyl, cycloalkenyl, cycloalkynyl, haloaryl, haloalkyl, aryl, alkaryl, aralkyl, alkoxyaryl, alkoxyalkyl, oligoalkoxyalkyl, aminoalkyl, mono- and di-alkylaminoalkyl, arylaminoalkyl, N-aryl-N-alkylaminoalkyl and aminoaryl, acyloxyalkyl, acylaminoalkyl, N-diacyl-iminoalkyl groups, hydroxyalkyl, hydroxyalkenyl, hydroxyalkynyl, hydroxyaryl, hydroxyalkoxyalkyl and hydroxy (oligoalkoxy)alkyl;

a group —$NHCONR^7R^8$ in which $R^7$ and $R^8$ are selected from the group consisting hydrogen, linear and branched alkyl, alkenyl, and alkynyl groups, cycloalkyl, cycioalkenyl, cycloalkynyl, haloaryl, haloalkyl, aryl, alkaryl, aralkyl, alkoxyaryl, alkoxyalkyl, oligoalkoxyalkyl, aminoalkyl, mono- and dialkylaminoalkyl, arylaminoalkyl, N-aryl-N-alkylaminoalkyl and aminoaryl, acyloxyalkyl, acylaminoalkyl, N-diacyl-iminoalkyl groups, hydroxyalkyl, hydroxyalkenyl, hydroxyalkynyl, hydroxyaryl, hydroxyalkoxyalkyl and hydroxy (oligoalkoxy)alkyl; or a polymeric moiety; and $R^4$ is an organosilyl group having the general formula (XIX)

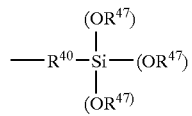

(XIX)

wherein each $R^{47}$ is selected from the group consisting of hydrogen, branched and straight $C_{1-12}$ alkyl, $C_{6-18}$ aryl, $C_{6-18}$ alkaryl, $C_{6-18}$ aralkyl, $C_{2-12}$ alkenyl and $C_{2-12}$ alkynyl;

$R^{40}$ is selected from the group consisting of a valence bond, branched and straight chain $C_{1-12}$ alkanediyl, straight and branched $C_{2-12}$ alkenediyl and straight and branched $C_{2-12}$ alkynediyl; and formula (XIX) is connected to the N atom of formula (I) through $R^{40}$.

19. An adduct according to claim 1 in which $R^4$ is an alkyl group having a substituent of the formula II as defined in claim 1.

20. An adduct according to claim 1 or claim 19 in which $R^3$ is alkylamino carbonyl or arylamino carbonyl substituted by isocyanate, a group $NHCOOR^6$ in which $R^6$ is selected from the group consisting hydrogen, linear and branched alkyl, alkenyl, and alkynyl groups, cycloalkyl, cycloalkenyl, cycloalkynyl, haloaryl, haloalkyl, aryl, alkaryl, aralkyl, alkoxyaryl, alkoxyalkyl, oligoalkoxyalkyl, aminoalkyl, mono- and di-alkylaminoalkyl, arylaminoalkyl, N-aryl-N-alkylaminoalkyl and aminoaryl, acyloxyalkyl, acylaminoalkyl, N-diacyl-iminoalkyl groups, hydroxyalkyl, hydroxyalkenyl, hydroxyalkynyl, hydroxyaryl, hydroxyalkoxyalkyl and hydroxy (oligoalkoxy)alkyl;

a group —$NHCONR^7R^8$ in which $R^7$ and $R^8$ are selected from the group consisting hydrogen, linear and branched alkyl, alkenyl, and alkynyl groups, cycloalkyl, cycloalkenyl, cycloalkynyl, haloaryl, haloalkyl, aryl, alkaryl, aralkyl, alkoxyaryl, alkoxyalkyl, oligoalkoxyalkyl, aminoalkyl, mono- and dialkylaminoalkyl, arylaminoalkyl, N-aryl-N-alkylaminoalkyl and aminoaryl, acyloxyalkyl, acylaminoalkyl, N-diacyl-iminoalkyl groups, hydroxyalkyl, hydroxyalkenyl, hydroxyalkynyl, hydroxyaryl, hydroxyalkoxyalkyl and hydroxy (oligoalkoxy)alkyl; or a polymeric moiety.

21. An adduct according to claim 20 in which $R^3$ is an alkylaminocarbonyl or arylamino carbonyl, substituted by a group $NHCONR^7R^8$ in which $R^7$ is an acyloxy-alkyl group and $R^8$ is hydrogen or $R^7$ is an (oligoalkoxy) alkyl group and $R^8$ is hydrogen.

22. A solution comprising an adduct according to claim 1 dissolved or dispersed in a solvent.

23. A method for the production of an adduct by the Michael-type addition of a zwitterionic reagent having the formula (XX)

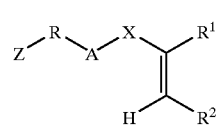

(XX)

with an amine reagent having the formula (XXI)

$H_2NR^{41}$ (XXI)

to form a zwitterion containing compound having the formula (XXII)

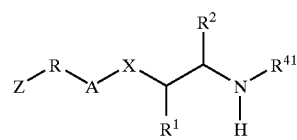

(XXII)

wherein

Z is a zwitterionic group with the general formula (IV);

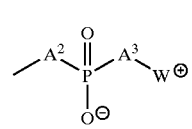

(IV)

in which the moieties $A^2$ and $A^3$, which are the same or different, are —O—, —S—, —NH— or a valence bond $W^+$ is a group of formula —$W^1$—$N^+R^{14}_3$, —$W^1$—$P^+R^{15}_3$, —$W^1$—$S^+R^{15}_2$ or —$W^1$—$Het^+$ in which:

$W^1$ is alkanediyl of 1 or more carbon atoms optionally containing one or more ethylenically unsaturated double or triple bonds, disubstituted-aryl (arylene), alkylene arylene, arylene alkylene, or alkylene aryl alkylene, cycloalkanediyl, alkylene cycloalkyl, cycloalkyl alkylene or alkylene cycloalkyl alkylene, which group $W^1$ optionally contains one or more fluorine substituents and/or one or more functional groups; and either the groups $R^{14}$ are the same or different and each is hydrogen or alkyl of 1 to 4 carbon atoms, or two of the groups $R^{14}$ together with the hetero atom to which they are attached form an aliphatic heterocyclic ring containing from 5 to 7 atoms, or the three groups $R^{14}$ together with the hetero atom to which they are attached form a fused ring structure containing from 5 to 7 atoms in each ring, and optionally one or more of the groups $R^{14}$ is substituted by a hydrophilic functional group, and the groups $R^{15}$ are the same or different and each is $R^{14}$ or a group $OR^{14}$, where $R^{14}$ is as defined above; or Het is an aromatic nitrogen-, phosphorus- or sulphur-containing ring;

A is O or $NR^6$ in which $R^6$ is hydrogen or a $C_{1-6}$ alkyl group;

X is an electron withdrawing group selected from the group consisting of carbonyl and sulphone groups, sulphonium and phosphonium salts;

R is selected from the group consisting of linear and branched alkanediyl, alkenediyl, alkynediyl, cycloalkanediyl, cycloalkenediyl, alkoxyalkylene, oligoalkosyalkylene, mono- or di-alkylaminoalkyl, N-arylamino alkylene, N-aryl-N-alkylaminoalkylene, $R^{41}$ is selected from the group consisting hydrogen, linear and branched alkyl, alkenyl and alkynyl groups, cycloalkyl, cycloalkenyl, cycloalkynyl, haloaryl, haloalkyl, aryl, alkaryl, aralkyl, hydroxyalkyl, hydroxyaryl, alkoxylaryl, alkoxylalkyl, oligoalkoxyalkyl, acyloxyalkyl, organosilane and organosiloxane groups any of which may be substituted by a group selected from amino, N-alkyl amino, N,N-dialkylamino, N-aryl-N-alkylamino and N-acylamino groups; and $R^1$ and $R^2$ are independently selected from hydrogen and $C_1$–$C_{12}$ alkyl groups.

24. The method according to claim 23, wherein $R^1$ and $R^2$ are selected from hydrogen or $C_1$–$C_4$ alkyl groups.

25. The method according to claim 23 or 24, wherein A is O.

26. The method of claim 23 in which $W^+$ is $W^1N^+R^{14}_3$ in which $W^1$ is a $C_{1-12}$ alkanediyl group.

27. The method of claim 23 in which X is C=O.

28. The method according to claim 23, wherein the zwitterionic containing compound of the formula (XXII) undergoes a second reaction with an isocyanate reagent of the formula (XXIII)

$$R^{42}\!-\!N\!=\!C\!=\!O \quad \text{(XXIII)}$$

wherein $R^{42}$ is selected from the group consisting of linear and branched alkyl, alkenyl, and alkynyl groups, alkoxycarbonyl, cycloalkyl, cycloalkenyl, cycloalkynyl, haloaryl, haloalkyl, aryl, alkaryl, aralkyl, alkoxyaryl, alkoxyalkyl, oligoalkoxyalkyl, di-alkylaminoalkyl, N-aryl-N-alkylaminoalkyl and acyloxy (including alkenoyloxy), acyloxyalkyl (including alkenoyloxyalkyl), N-diacyl-iminoalkyl groups, organosilane and organosiloxane groups and any of the above groups substituted with a zwitterionic group Z or an isocyanate group, to form a compound having the formula (XXIV)

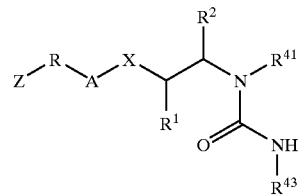

(XXIV)

in which $R^{43}$ is the same as $R^{42}$ or, where $R^{42}$ comprises an isocyanate group, may be the corresponding group formed by reaction of the isocyanate group with a compound having an active hydrogen atom present in the second reaction mixture (including the zwitterionic containing compound, a hydroxyl group containing compound or a primary or secondary amine group containing compound).

29. The method according to claim 28, wherein the isocyanate of the formula (XXIII) is selected from the group consisting of $C_{2-30}$ alkyl-, $C_{6-30}$ aryl- and $C_{6-20}$ alicyclic-mono-isocyanates or diisocyanates, allyl isocyanate, isocyanato $C_2C_{28}$-alkylacrylates, $C_2$–$C_{28}$-isocyanato alkylmethacrylates.

30. The method according to claim 29 in which the isocyanate is selected from the group consisting of allyl isocyanate, dimethyl metaisopropenylbenzylisocyanate, isocyanatoethylmethacrylate, isophorone diisocyanate, hexamethylene diisocyanate, dicyclohexyl methane diisocyanate and meta-tetramethylxylylene diisocyanate.

31. A method according to claim 29 or claim 30 in which the isocyanate is a di-isocyanate and in which the isocyanate is present in molar amount more than 0.5× the molar amount of the zwitterion containing compound and in which isocyanate groups which do not react with the zwitterion containing compound are reacted simultaneously or subsequently with an additional active hydrogen containing compound, selected from primary and secondary mono- and di-amines, and mono- and di-hydroxyl group containing compounds, and mixtures thereof.

32. A method according to claim 31 in which the additional active hydrogen containing compound is selected from $C_{2-24}$ alkanediamine, mono- and di-amine-terminated poly ($C_2$ or $C_3$ alkylene glycol), $C_{2-24}$ alkanediols and N-alkylaminoalkyl(meth)acrylates, and $C_{2-6}$ hydroxyalkyl (meth)-acrylates and -acrylamides.

33. A method according to claim 23 in which the group $R^{41}$ is an organosilyl group of the formula XXV

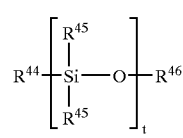

XXV in which one of the groups $R^{44}$ or $R^{45}$ is a divalent moiety selected from the group consisting of a valence bond, $C_{1-12}$-alkenediyl, $C_{2-12}$ alkenediyl, $C_{2-12}$-alkynediyl and the remaining groups $R^{44}$, $R^{45}$ and $R^{46}$ are monovalent moieties independently selected from straight and branched $C_{1-12}$ alkyl, $C_{2-12}$ alkenyl, $C_{2-12}$ alkynyl, $C_{6-24}$ alkanyl, $C_{6-24}$ aryalkyl and aryl, any of which groups may be substituted by one or more amino, N-alkylamino, N,N-dialkylamino, N-alkyl-N-arylamino or N-arylamino groups; and t is 1 to 300.

34. A method according to claim 33 in which $R^{44}$ is a $C_{2-6}$ alkanediyl, each of the groups $R^{45}$ is methyl, $R^{46}$ is an amino substituted $C_{2-6}$ alkyl group and t is in the range 5 to 50.

35. A method for the production of an adduct by the Michael-type addition of a zwitterionic reagent having the formula (XX)

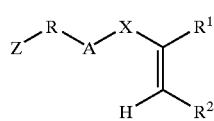

(XX)

with an amine reagent having the formula (XXI)

 (XXI)

to form a zwitterion containing compound having the formula (XXII)

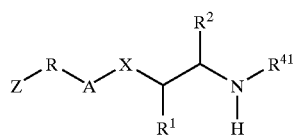

(XXII)

wherein
Z is a zwitterionic group;
A is O or $NR^6$ in which $R^6$ is hydrogen or a $C_{1-6}$ alkyl group;
X is an electron withdrawing group selected from the group consisting of carbonyl and sulphone groups, sulphonium and phosphonium salts;
R is selected from the group consisting of linear and branched alkanediyl, alkenediyl, alkynediyl, cycloalkanediyl, cycloalkenediyl, alkoxyalkylene, oligoalkosyalkylene, mono- or di-alkylaminoalkyl, N-arylamino alkylene, N-aryl-N-alkylaminoalkylene,
$R^{41}$ is a group of formula XXVI

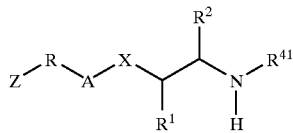

XXVI wherein each group $R^{33}$ is independently selected from the group consisting of hydrogen, $C_{1-6}$ alkyl, $C_{6-18}$ aryl, $C_{6-18}$ aralkyl, $C_{6-18}$ alkaryl and $C_{2-6}$ alkenyl;
each group $R^{34}$ is independently selected from the group consisting of hydrogen, $C_{1-6}$ alkyl, $C_{6-18}$ aryl, $C_{6-18}$ aralkyl, $C_{6-18}$ alkaryl and $C_{2-6}$ alkenyl;
$R^{35}$ is a divalent moiety selected from the group consisting of a valence bond, $C_{1-6}$ alkanediyl, $C_{6-18}$ arylene, $C_{6-18}$ aralkylene, $C_{2-6}$ alkenediyl, mono-, di- and tri-alkylaminoalkyl, arylaminoalkyl, arylaminoaryl, N-aryl-N-alkylaminoalkyl and N-aryl-N-alkylaminoaminoaryl;
$R^{47}$ is selected from the same groups as $R^{33}$, or is $C_{1-12}$ alkyl substituted by an amino, N-alkylamino, N,N-dialkylamino N-arylamino or N-aryl-N-alkylamino group;
u is 0 or an integer in the range 1–10,
v is 0 or an integer of in the range 1–500; and
XXVI has a formula weight of 100–10000.

36. A method for the production of an adduct by the Michael-type addition of a zwitterionic reagent having the formula (XX)

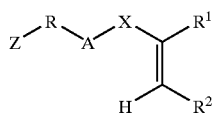

(XX)

with an amine reagent having the formula (XXI)

 (XXI)

to form a zwitterion containing compound having the formula (XXII)

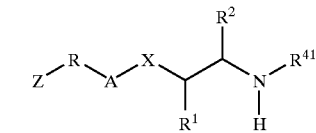

(XXII)

wherein
Z is a zwitterionic group;
A is O or $NR^6$ in which $R^6$ is hydrogen or a $C_{1-4}$ alkyl group;
X is an electron withdrawing group selected from the group consisting of carbonyl and sulphone groups, sulphonium and phosphonium salts;
R is selected from the group consisting of linear and branched alkanediyl, alkenediyl, alkynediyl, cycloalkanediyl, cycloalkenediyl, alkoxyalkylene, oligoalkosyalkylene, mono- or di-alkylaminoalkyl, N-arylamino alkylene, N-aryl-N-alkylaminoalkylene,
$R^{41}$ is a group of the general formula (XIX)

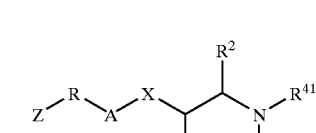

(XIX)

wherein each $R^{47}$ is selected from the group consisting of hydrogen, branched and straight $C_{1-12}$ alkyl, $C_{6-18}$ aryl, $C_{6-18}$ alkaryl, $C_{6-18}$ aralkyl, $C_{2-12}$ alkenyl and $C_{2-12}$ alkynyl;
$R^{40}$ is selected from the group consisting of a valence bond, branched and straight chain $C_{1-12}$ alkanediyl, straight and branched $C_{2-12}$ alkenediyl and straight and branched $C_{2-12}$ alkynediyl; and
(XIX) is connected to the N atom of (XXI) through $R^{40}$.

37. The method according to claim 23, wherein the Michael-type addition reaction is carried out in a solventless system.

38. The method according to claim 23, wherein the Michael-type addition reaction is carried out in the presence of a solvent selected from $C_{1-8}$, secondary $C_{1-8}$ or tertiary alcohols.

39. The method according to claim 38, wherein the alcohol is selected from isopropanol, isobutanol, tertbutanol and hydroxyethylmethacrylate.

40. A polymer produced by polymerisation of an adduct according to claim 1, wherein the adduct is polymerised through a reactive group on $R^3$.

41. A polymer according to claim 40 produced by the homo-polymerisation or co-polymerisation of an adduct wherein $R^3$ comprises an ethylenically unsaturated group.

42. A polymer according to claim 41, produced by a polymerisation process selected from free radical, cationic, anionic and metal catalysed polymerizations.

43. A polymer according to claim 41 or claim 42 in which the adduct is copolymerised with ethylenically unsaturated comonomer.

44. A polymer according to claim 40 wherein the reactive group on $R^3$ is an isocyanate group, the adduct comprises more than one isocyanate group, and polymerisation involves the reaction with one or more di-functional amine or alcohol monomers to form a polyurea or polyurethane compound.

45. A process for coating a surface comprising applying a composition according to claim 22 to the surface of a polymer or metal and substantially curing the composition to leave a solid coating on the surface.

46. A process according to claim 45, wherein the surface is a functional surface capable of forming at least one covalent bond with a reactive group on $R^3$ of the adduct in which the curing step is carried out under conditions whereby the covalent bond is formed.

47. A process according to claim 45, wherein the adduct is a polymerisable compound and the curing step involves polymerising the adduct.

48. A polymerisation process comprising the homo-polymerisation or copolymerisation of an adduct according to claim 1 having a polymerisable reactive group in $R^3$.

49. An article comprising a polymer according to claim 40.

50. An article according to claim 49, which is a contact lens.

51. An article according to claim 50, wherein $R^4$ comprises an organosiloxyl moiety.

52. A zwitterion containing adduct having the formula (I)

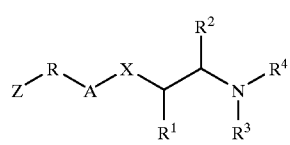

(I)

wherein

Z is a zwitterionic group;

X is an electron withdrawing group selected from the group consisting of carbonyl and sulphone groups, sulphonium and phosphonium salts;

R is selected from the group consisting of linear and branched alkanediyl, alkenediyl, alkynediyl, cycloalkanediyl, cycloalkenediyl, cycloalkynediyl, arylene, alkarylene, aralkylene, alkoxyarylene, alkoxyalkyl, oligo(alkoxy)alkyl, mono- and di-alkylaminoalkyl N-arylaminoalkyl, N-aryl-N-alkylaminoalkyl; $R^1$ and $R^2$ are independently selected from hydrogen and $C_1$–$C_{12}$ alkyl groups; A is O or $NR^6$, where $R^6$ is selected from the group consisting of hydrogen and $C_{1-6}$ alkyl;

$R^3$ is alkylamino carbonyl or arylamino carbonyl substituted by
isocyanate,
a group $NHCOOR^6$ in which $R^6$ is selected from the group consisting hydrogen, linear and branched alkyl, alkenyl, and alkynyl groups, cycloalkyl, cycloalkenyl, cycloalkynyl, haloaryl, haloalkyl, aryl, alkaryl, aralkyl, alkoxyaryl, alkoxyalkyl, oligoalkoxyalkyl, aminoalkyl, mono- and di-alkylaminoalkyl, arylaminoalkyl, N-aryl-N-alkylaminoalkyl and aminoaryl, acyloxyalkyl, acylaminoalkyl, N-diacyl-iminoalkyl groups, hydroxyalkyl, hydroxyalkenyl, hydroxyalkynyl, hydroxyaryl, hydroxyalkoxyalkyl and hydroxy (oligoalkoxy)alkyl; or a group $—NHCONR^7R^8$ in which $R^7$ and $R^8$ are selected from the group consisting hydrogen, linear and branched alkyl, alkenyl, and alkynyl groups, cycloalkyl, cycioalkenyl, cycloalkynyl, haloaryl, haloalkyl, aryl, alkaryl, aralkyl, alkoxyaryl, alkoxyalkyl, oligoalkoxyalkyl, aminoalkyl, mono- and dialkylaminoalkyl, arylaminoalkyl, N-aryl-N-alkylaminoalkyl and aminoaryl, acyloxyalkyl, acylaminoalkyl, N-diacyl-iminoalkyl groups, hydroxyalkyl, hydroxyalkenyl, hydroxyalkynyl, hydroxyaryl, hydroxyalkoxyalkyl and hydroxy (oligoalkoxy)alkyl; or $R^3$ is an alkylaminocarbonyl or arylamino carbonyl, substituted by a group $NHCONR^7R^8$ in which $R^7$ is an acyloxy-alkyl group and $R^8$ is hydrogen or $R^7$ is an (oligoalkoxy) alkyl group and $R^8$ is hydrogen; and $R^4$ is selected from the group consisting hydrogen, linear and branched alkyl, alkenyl, and alkynyl groups, alkoxycarbonyl, alkylaminocarbonyl, cycloalkyl, cycloalkenyl, cycloalkynyl, haloaryl, haloalkyl, aryl, alkaryl, aralkyl, alkoxyaryl, alkoxyalkyl, oligoalkoxyalkyl, aminoalkyl, mono- and di-alkylaminoalkyl, arylaminoalkyl, N-aryl-N-alkylaminoalkyl and -aminoaryl, acyloxy, acyloxyalkyl, acylaminoalkyl, N-diacyl-iminoalkyl groups, mono- and di-alkylaminocarbonyl, organosilyl, arylamino carbonyl, aryl(alkyl)amino carbonyl, and organosiloxyl groups and any of the above groups substituted with a group II

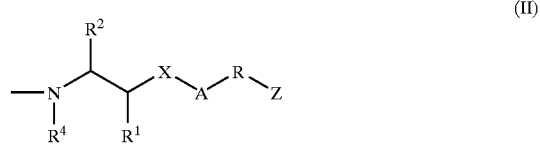

(II)

in which the groups R, $R^1$, $R^2$, $R^4$, Z and A are the same as in (I);

a group III

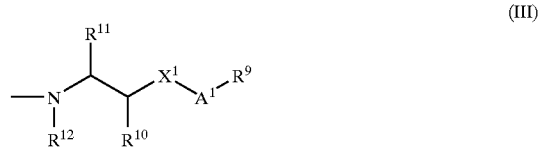

(III)

in which $A^1$ is O or $NR^3$ where $R^{13}$ is hydrogen or $C_{1-6}$ alkyl;

$X^1$ is an electron withdrawing group selected from carbonyl, sulphonyl, sulphonium and phosphonium groups;

$R^{12}$ is H or $C_{1-6}$ alkyl;

$R^{10}$ and $R^{11}$ are independently selected from H and $C_{1-4}$ alkyl; and $R^9$ is optionally substituted alkyl or aryl;

a reactive group; or a polymeric moiety.

53. A method for the production of an adduct by the Michael-type addition of a zwitterionic reagent having the formula (XX)

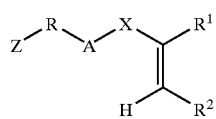

(XX)

with an amine reagent having the formula (XXI)

$H_2NR^{41}$ (XXI)

to form a zwitterion containing compound having the formula (XXII)

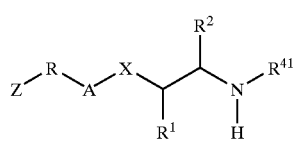

(XXII)

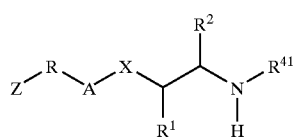

(XXII)

wherein Z is a zwitterionic group;
A is O or $NR^6$ in which $R^6$ is hydrogen or a $C_{1-6}$ alkyl group;
X is an electron withdrawing group selected from the group consisting of carbonyl and sulphone groups, sulphonium and phosphonium salts;
R is selected from the group consisting of linear and branched alkanediyl, alkenediyl, alkynediyl, cycloalkanediyl, cycloalkenediyl, alkoxyalkylene, oligoalkosyalkylene, mono- or di-alkylaminoalkyl, N-arylamino alkylene, N-aryl-N-alkylaminoalkylene,
$R^{41}$ is selected from the group consisting hydrogen, linear and branched alkyl, alkenyl and alkynyl groups, cycloalkyl, cycloalkenyl, cycloalkynyl, haloaryl, haloalkyl, aryl, alkaryl, aralkyl, hydroxyalkyl, hydroxyaryl, alkoxylaryl, alkoxylalkyl, oligoalkoxyalkyl, acyloxyalkyl, organosilane and organosiloxane gropus any of which may be substituted, by a group selected from amino, N-alkyl amino, N,N-dialkylamino, N-aryl-N-alkylamino and N-acylamino groups; and $R^1$ and $R^2$ are independently selected from hydrogen and $C_1$–$C_{12}$ alkyl groups, wherein the zwitterionic containing compound of the formula (XXII) undergoes a second reaction with an isocyanate reagent of the formula (XXIII)

$R^{42}-N=C=O$ (XXIII)

wherein $R^{42}$ is selected from the group consisting of linear and branched alkyl, alkenyl, and alkynyl groups, alkoxycarbonyl, cycloalkyl, cycloalkenyl, cycloalkynyl, haloaryl, haloalkyl, aryl, alkaryl, aralkyl, alkoxyaryl, alkoxyalkyl, oligoalkoxyalkyl, di-alkylaminoalkyl, N-aryl-N-alkylaminoalkyl and acyloxy (including alkenoyloxy), acyloxyalkyl (including alkenoyloxyalkyl), N-diacyl-iminoalkyl groups, organosilane and organosiloxane groups and any of the above groups substituted with a zwitterionic group Z or an isocyanate group, to form a compound having the formula (XXIV)

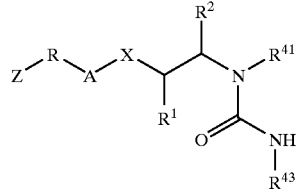

(XXIV)

in which $R^{43}$ is the same as $R^{42}$ or, where $R^{42}$ comprises an isocyanate group, may be the corresponding group formed by reaction of the isocyanate group with a compound having an active hydrogen atom present in the second reaction mixture.

* * * * *